US012161577B2

(12) United States Patent
Tate Morgan et al.

(10) Patent No.: US 12,161,577 B2
(45) Date of Patent: Dec. 10, 2024

(54) INFLATABLE CERVICAL COLLAR NECK SYSTEM

(71) Applicant: Tate Technology, LLC, Pacific Palisades, CA (US)

(72) Inventors: Jenny Tate Morgan, Pacific Palisades, CA (US); Richard M. Jensen, Parker, TX (US); Acen Jordan, Carmel, CA (US)

(73) Assignee: TATE TECHNOLOGY, LLC, Pacific Palisades, CA (US)

(*) Notice: Subject to any disclaimer, the term of this patent is extended or adjusted under 35 U.S.C. 154(b) by 85 days.

(21) Appl. No.: 17/828,605

(22) Filed: May 31, 2022

(65) Prior Publication Data

US 2022/0287865 A1 Sep. 15, 2022

Related U.S. Application Data

(63) Continuation-in-part of application No. 16/688,852, filed on Nov. 19, 2019, now abandoned.

(60) Provisional application No. 63/194,806, filed on May 28, 2021, provisional application No. 62/769,955, filed on Nov. 20, 2018.

(51) Int. Cl.
*A61F 5/055* (2006.01)
*A61B 5/00* (2006.01)
*A61F 5/058* (2006.01)

(52) U.S. Cl.
CPC ........ *A61F 5/05816* (2013.01); *A61B 5/6812* (2013.01); *A61F 5/055* (2013.01)

(58) Field of Classification Search
CPC ..... A61F 5/05816; A61F 5/055; A61B 5/6812
See application file for complete search history.

(56) References Cited

U.S. PATENT DOCUMENTS

| | | | | |
|---|---|---|---|---|
| 2,806,471 A | * | 9/1957 | Breese | A61F 5/055 602/17 |
| 3,164,151 A | * | 1/1965 | Vere Nicoll | A61F 5/05816 602/18 |
| 3,765,412 A | * | 10/1973 | Ommaya | A61F 5/055 128/DIG. 20 |
| 3,921,626 A | * | 11/1975 | Neel | A61F 5/055 602/18 |
| 4,745,922 A | * | 5/1988 | Taylor | A61F 7/02 607/104 |
| 5,390,367 A | | 2/1995 | Rush | |
| 5,403,266 A | * | 4/1995 | Bragg | A61F 5/055 602/5 |

(Continued)

OTHER PUBLICATIONS

International Search Report and Written Opinion issued in PCT/US22/31562.

(Continued)

*Primary Examiner* — Quang Pham
(74) *Attorney, Agent, or Firm* — Jeffer Mangels Butler & Mitchell LLP; Brennan C. Swain, Esq.

(57) ABSTRACT

A cervical collar system that includes a collar assembly that includes a wall member having an inner side and an outer side and a bladder member secured on the inner side of the wall member. The collar assembly includes an open position and a closed position and is configured to be received on the neck of a wearer. The cervical collar system also includes a first pump assembly in fluid communication with the bladder member.

1 Claim, 13 Drawing Sheets

(56) References Cited

U.S. PATENT DOCUMENTS

| | | | |
|---|---|---|---|
| 5,454,781 A * | 10/1995 | Chitwood | A61F 5/055 606/240 |
| 5,546,609 A | 8/1996 | Rush | |
| 5,628,065 A | 5/1997 | Austin | |
| 5,752,927 A * | 5/1998 | Rogachevsky | A61F 5/012 602/18 |
| 6,050,965 A * | 4/2000 | Pillai | A61F 5/055 602/18 |
| 6,447,468 B1 * | 9/2002 | Hankins | A61F 5/055 128/845 |
| 6,826,781 B2 | 12/2004 | Lewis | |
| 6,857,136 B1 * | 2/2005 | Bradley | A41D 13/0125 441/106 |
| 6,921,376 B2 * | 7/2005 | Tweardy | A61F 5/055 602/18 |
| 7,048,705 B2 * | 5/2006 | Pillai | A61F 5/012 602/18 |
| 7,070,573 B2 * | 7/2006 | Axelsson | A61F 5/055 128/845 |
| 7,128,724 B2 * | 10/2006 | Marsh | A61F 5/055 602/17 |
| 7,146,665 B1 * | 12/2006 | Moorin | A47C 7/383 5/639 |
| 7,182,082 B2 * | 2/2007 | Hoffrichter | A61F 5/055 601/39 |
| 7,670,307 B2 * | 3/2010 | Chitwood | A61H 1/0296 128/869 |
| 8,038,635 B2 * | 10/2011 | Dellanno | A61F 5/055 602/17 |
| 8,118,761 B2 * | 2/2012 | Rogachevsky | A61H 1/0296 601/39 |
| 8,127,373 B1 | 3/2012 | Fodemski | |
| 8,251,939 B2 * | 8/2012 | Aune | A61H 1/0296 602/18 |
| 8,303,626 B2 * | 11/2012 | Fischer | A61F 5/055 606/241 |
| 8,491,512 B2 * | 7/2013 | Donaldson | A61F 5/055 602/18 |
| 8,905,958 B2 * | 12/2014 | Senyei | A61F 5/055 602/18 |
| 9,486,354 B2 * | 11/2016 | Maher | A61B 5/6812 |
| 9,986,777 B2 | 6/2018 | Morgan | |
| 10,117,768 B1 * | 11/2018 | Freed | A61F 5/055 |
| 10,406,397 B1 * | 9/2019 | Graham | A61F 5/05883 |
| 11,696,766 B2 * | 7/2023 | Smith | A61B 90/08 606/202 |
| 2002/0100109 A1 | 8/2002 | Hoop | |
| 2003/0060744 A1 * | 3/2003 | Caille | A61F 5/055 602/18 |
| 2004/0183283 A1 | 9/2004 | Buckman | |
| 2005/0067816 A1 | 3/2005 | Buckman | |
| 2006/0015048 A1 * | 1/2006 | Pillai | A61F 5/012 602/18 |
| 2006/0047229 A1 * | 3/2006 | Dussaussoy | A61H 1/0296 601/79 |
| 2006/0107952 A1 | 5/2006 | Schlosser | |
| 2006/0217648 A1 * | 9/2006 | Rogachevsky | A61F 5/05816 602/18 |
| 2007/0075528 A1 | 4/2007 | Makabe | |
| 2008/0004556 A1 * | 1/2008 | Gehlbach | A61F 5/055 602/18 |
| 2009/0149788 A1 * | 6/2009 | Dellanno | A61F 5/055 602/18 |
| 2009/0239428 A1 | 9/2009 | Berchten | |
| 2009/0247918 A1 * | 10/2009 | Patron | A61F 5/055 602/18 |
| 2009/0254003 A1 | 10/2009 | Buckman | |
| 2010/0259471 A1 | 10/2010 | Takano | |
| 2010/0317930 A1 * | 12/2010 | Oexman | A47C 31/123 600/300 |
| 2010/0318239 A1 * | 12/2010 | Oexman | A47C 23/0435 5/709 |
| 2011/0010014 A1 * | 1/2011 | Oexman | F24F 11/63 600/301 |
| 2011/0172579 A1 * | 7/2011 | Chiu | A61N 5/0625 602/36 |
| 2011/0291842 A1 * | 12/2011 | Oexman | G08B 21/06 340/575 |
| 2012/0011642 A1 | 1/2012 | Dainese | |
| 2012/0143110 A1 * | 6/2012 | Maher | A61F 5/055 602/14 |
| 2012/0310483 A1 * | 12/2012 | Lanter | B60R 22/48 24/593.1 |
| 2013/0060168 A1 | 3/2013 | Chu | |
| 2014/0094727 A1 | 4/2014 | Deshpante | |
| 2014/0210626 A1 * | 7/2014 | Kresser | A61M 21/00 340/575 |
| 2015/0018733 A1 | 1/2015 | Ben-Meir | |
| 2015/0190266 A1 * | 7/2015 | Hollern | A61F 5/055 602/18 |
| 2015/0374060 A1 | 12/2015 | Morgan | |
| 2017/0000359 A1 | 1/2017 | Kohli | |
| 2017/0020722 A1 * | 1/2017 | Maher | A61B 5/6812 |
| 2017/0109131 A1 | 4/2017 | Boesen | |
| 2017/0127858 A1 | 5/2017 | Teh et al. | |
| 2017/0270464 A1 | 9/2017 | Morgenthau | |
| 2018/0000367 A1 | 1/2018 | Longinotti-Buitoni | |
| 2018/0000627 A1 * | 1/2018 | Islava | F04B 53/10 |
| 2019/0132948 A1 | 5/2019 | Longinotti-Buitoni et al. | |
| 2019/0350739 A1 * | 11/2019 | Maher | A61F 7/0085 |
| 2019/0350740 A1 * | 11/2019 | Maher | A61F 5/055 |
| 2020/0154799 A1 * | 5/2020 | Morgan | A61B 5/1112 |
| 2022/0066500 A1 * | 3/2022 | Vankipuram | G06F 3/015 |

OTHER PUBLICATIONS

International Search Report and Written Opinion issued in PCT/US14/19926.

International Search Report and Written Opinion issued in PCT/US19/62271.

* cited by examiner

INFLATABLE CERVICAL COLLAR NECK SYSTEM

CROSS-REFERENCE TO RELATED APPLICATIONS

This application is a continuation-in-part of U.S. patent application Ser. No. 16/688,852, filed Nov. 19, 2019, which claims the benefit of U.S. Provisional Application No. 62/769,955, filed Nov. 20, 2018. This application also claims the benefit of U.S. Provisional Application No. 63/194,806, filed on May 28, 2021. All applications listed above are incorporated by reference herein in their entireties.

FIELD OF THE INVENTION

The present invention relates generally to a cervical collar neck system, and more particularly to an inflatable cervical collar neck system that can be used in health, military and medical applications.

BACKGROUND OF THE INVENTION

Traditional or conventional cervical collars are used and have primarily one element for function, or one function, which is for neck support post trauma or surgery or both, whether from accidents, long-standing issues, or incidents. Manufacturers' cervical collars typically cover some portion of the neck, or all of the neck, and some portion of the upper cervical vertebrae. They are designed to support the neck in a chin-up to level with the ground position, head forward, and are generally worn post-surgery, post use of a halo, post muscle and tissue damage of the neck area.

Conventional cervical collars are often hard plastic and are wrapped around or closing around the wearer's neck, and do not always fit perfectly with all the ranges of neck sizes from children's necks to exceptionally large male neck sizes. These typically close using Velcro, have some adjustment capability, and some may have some air sacs. Some other cervical collars are made of strictly foam with an outer exterior material, and these wrap around the neck and close typically with Velcro.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

Presently, the prior art surrounds hard plastic health cervical collars or foam collars, or a combination of plastic intermingled with small air pocket(s). The present invention provides an inflatable health and military medical cervical collar neck supportive system(s) using a PVC film bladder compression system with an exterior plastic, aluminum, or potentially other materials insert designed to act as a tension wall/cylinder system housed in a separate, but attached PVC Film exterior pocket with the present invention in two formats—the first being an all plastic design enabling it to remain on the patient going straight to imaging at the hospital—imaging including, but not limited to CT Scans, x-rays, and MRI's, and which may be used on the military battlefield with a gas canister inflation battery activated system with a spring loaded solenoid system to pierce and release the $CO_2$ gas canister versus a pump system. The second inflatable health and military medical cervical collar neck supportive system(s) has/have all electronics sensor housed over the wearer's carotid artery capable of reading biometrics in real-time tracking and communicates with your doctors key vital bio-metric information using a sensor puck, has a full electronic control system mother board, algorithms designed to maintain desired psi pressure using a maintenance pump, a control board on a "tether" or "dongle" with LED red, yellow and green for go-no-go indicator lights for system readiness and blue LED lights for system charge along with two "system status" buttons for increasing/decreasing the psi pressure and emergency rapid deflate if both buttons are pressed simultaneously all contained on one exterior to the cervical collar system tether/dongle, as well as all the functions on the tether/dongle will also be on the detachable pump/motor system with a quick disconnect system in a readable format, a sensor puck to capture and transmit bio-metric data, a battery, flex wiring, regular wiring, ribbon wiring, Bluetooth, GPS, 5 g phone capability, a separate detachable pump motor contained in the detachable inflation housing that may be charged via the USB port or a wall jack, a two-way port valve that seals the cervical collar bladder, and a magnetized front clip closure locking system(s) that reside above and below the front trachea opening, plus a non-magnetized for the CT Scan version of all plastic front closure locking system. Additionally, there is a manifold, solenoid value, a back-up pump, battery, communication with your doctor of biometrics in real-time, and ability to remote inflate to pre-determined settings by your doctor of psi pressure in the bladder. The system works with an App using a Web-based portal, and/or existing/new and loaded software on provided or purchased hardware i.e. tablets, phones, and prospectively watches or other devices.

Additionally, the present invention includes heart rate (HR), $SPO^2$, pulse, heart rate variability, fall detection capability, future EKG/ECG, Blood Pressure, and bio-metric alerts that can be sent to doctors, etc. that are built into the programming. The front closure locking system that is 100% plastic for the CT Scan, or for complete electronic systems set up using a magnetic closure support system for the sensor systems that are easily closed and opened by the wearer or the attending doctor/physician/military medic, a tracheotomy opening ready for doctors to insert a trachea tube for breathing when required for the patient. Also the system has flex circuits/ribbons/wires going around the cervical collar on the exterior of the "tension" wall go to and from the electronics, also connecting all electronic and functioning component parts, inflation tubes, tether/dongle, detachable pump motor, also connecting the sensor that is positioned on the interior (compression) next to the wearers neck (carotid artery), battery and all electronic systems, and a "manifold assembly" that contains: pressure sensor small maintenance pump, check value(s), solenoid valve, hose connector, a release valve, and more. All major electronics are housed on the back of the bladder/back of the wearer on the exterior tension wall and will contain the battery with the main computer board, along with the manifold assembly, and immediately below the back-up pump motor. The sensor is located on the inside of the bladder next to the wearer's carotid artery. Exterior components are the detachable pump motor and LED read-out screen, the bladder valve import, as well as the attached dongle. The 100% plastic bladder may also have honeycomb cells on the inside, or exterior of the bladder containing cooling gel that may be kept cold in a refrigeration system or in an ice cooler in the paramedics trucks and ambulances, as ice and coolness addresses swelling of spinal injuries including muscle, ligament, tendon, and the spinal cord directly, and is of benefit in transportation to the hospital to address injury inflammation. Additionally, cooling wicking material as an outer cover to the bladder will also address swelling to a degree. Latex-free materials will be used in outer covering(s) on the bladder. There may be a permanent inner exterior cover, which is not to be removed where the electronic component parts will be attached, as well as all wiring will be protected in tubes/channels of the same material, which may be latex-free material. There may be a second outer latex-free cover that is removable and washable with viewing windows for the electronic component parts, as well as the opening for the sensor on the inside, so it may be touching the wearers skin, and will have openings for the detachable pump and the dongle to be on the exterior.

Regarding the military version, communication while in battle or hostile environments will be designed so as the GPS is not able to be tracked, or all 100% plastic versions will be used to transport to the military on-field medical facilities or hospitals with electronic versions used in the hospital. The system works with an App using a Web-based portal, and/or existing/new and loaded software on provided or purchased hardware i.e. tablets, phones, and prospectively watches or other devices. The military health collar neck system may or may not have the health sensor system or may have the health sensor with the data captured, but not transmitted in real-time, and may be downloaded at a later time due to battlefield considerations of GPS tracking by the enemy. The health, as well as the military cervical collar neck system(s) are designed to protect and support the human neck post injury to the neck area from base of the skull, or occipital bone down through the cervical vertebrae to the beginning thoracic vertebrae, from the temporal bone to the shoulders, clavicle and sternum. This system will not support injuries to the middle of the back or below thoracic 1 into the lumbar vertebrae resulting from accidents that impact the thoracic into lumbar region. The system is designed to support the neck from cervical or C1 down to C7/T1 addressing cervical vertebrae injuries, as well as support the neck for non-skeletal ligament, tendon and soft tissue damage by use of compression of the bladder system with an outer tension wall/cylinder. The system addresses neck support linearly front to back, side to side, diagonally, plus rotationally, providing structure and support fitting snugly to the wearer's neck from the occipital bone in the base of the skull down through the cervical vertebrae, from the ear lobes and temporal bone to the shoulder region and trapezius muscles, from the sternum and clavicle bones up to the lower mandible jaw.

The health cervical collar 100% plastic bladder system is to be used for patient stabilization and transport to the hospital, for all related neck tissue and skeletal injuries, taken directly to imaging equipment at the hospital, and inflates using a detachable motor/pump system inflating with ambient air to fit the wearer's neck using an all or 100% plastic port, bladder and closure system. The post imaging sensor system health cervical collar all electronics system contains a separate maintenance motor and pump to sustain the desired pressure or psi and total volume with two settings specified per neck circumference size and prescribed/suggested by your doctor. Once at the hospital, using the 100% all plastic version of the health cervical or military bladder, and at the imaging department of the hospital then the detachable pump/motor (military will use a $CO_2$ gas canister) may be disconnected immediately before being imaged. The military cervical collar bladder system will also have two versions, and the all plastic version will inflate using a $CO_2$ gas cartridge that will be housed in the detachable and separate inflation housing and will be used to transport to imaging, and the canister may be removed immediately before being imaged. The post imaging sensor system military cervical collar will inflate using a detachable pump/motor with a maintenance motor to maintain the desired pressure or psi and total volume with two settings specified per neck circumference size and prescribed by the military medic or military doctor, to fit the wearer's neck.

For both health and military cervical collar applications the present invention monitors the wearer directly via the sensor system, algorithms, with real-time data transmission via GPS, Bluetooth and 5 g, also via the detachable pump motor and dongle, and remotely provides the information in real-time to your App, and directly to your doctor, as well as communicates psi or pressure ratings of the bladder in the cervical collar, key vitals in real-time from the bio-metric sensor arrangement system in which blood pressure, oxygen saturation rate, pulse, pitching/fall detection, EKG, heart rate variability, and more that requires monitoring by the doctor of the wearer while wearing this cervical apparatus support device. Both the health and military system are extremely light weight and flat easily carried by EMT or paramedics for civilians use, and then in the military for medics carrying onto the battlefield, and since the system is already assembled it may be pulled out of the EMT or medics bag, placed around the wearers neck and immediately inflated by the detachable pump for the health version, and for the military version by pulling the tab from the battery releasing the $CO_2$ gas. The 100% plastic are disposable and will have an inner layer of exterior latex-free material for comfort and a removable outer layer if required. The full sensor system collars will also have an inner exterior latex-free layer of material with TPU brackets containing/housing the manifold, mother board, all electronics, the battery, and more sewn into/onto the inner wicking material layer, as well as there will be an inside bracket at the wearers neck/skin at the carotid artery either left or right side that will house the puck/sensor (that is reusable) to read the wearer's vitals. Plus, the full sensor system will have a removable outer exterior layer of cooling wicking material to warm wicking material available depending upon the region of the globe where the wearer resides, i.e. warm weather such as Florida and cold such as Montana as examples that is washable. The health cervical collar inflatable neck supportive system will also have a washable fully exterior wicking material that may be removed and cleaned and reused in the sensor system bladder, and there will be a window in the material, so that the electronics on the back exterior may be viewed, as well as an opening for the sensor. The electronics will be encapsulated in protective plastic conformal coding protection, so it is 100% sealed and enclosed, and safe from the environment and being bumped or hit.

In accordance with a first aspect of the present invention there is provided a health and military cervical collar system(s) configured to be received on the neck of a wearer that includes a compression bladder and tension wall/cylinder interior member system, that includes a neck portion, a lower mandible portion, a clavicle portion, a sternum portion, a cervical vertebrae into thoracic vertebrae portion, a right and left trapezius portion, and up to the base of the occipital bone portion, and up to the right side and left side temporal bone above the earlobes portion, a sensor system or sensor arrangement system that includes at least one gyro sensor, and at least one accelerometer sensor, and at least one health sensor system positioned next to the wearer's neck on the interior member, a sewn material housing the cervical collar bladder system, a washable exterior gaiter member using latex-free cooling wicking material, or a normal latex-free wicking material, or warmer latex-free wicking material, a first pump and motor system to inflate the health bladder, a $CO_2$ inert gas canister for the military system, and a second pump maintenance motor system to maintain desired psi pressure for both the health and military bladder system(s), an manifold and solenoid actuation system in electrical communication with the sensor system, at least one battery system, a Bluetooth system, a GPS system, a 5 g voice communication system, a mother and daughter electronic boards system, wires, flex wires, ribbon wires, flex circuits, LED indicator lights for battery charge, LED indicator lights for go-no-go readiness, rapid deflation buttons all contained on a tether/dongle system, readiness indicators on the detachable pump and $CO_2$ systems, and whether or not the system is locked and magnetically locked and connected to the full electronics systems and ready for inflation, achieving the targeted desired psi inflation volumes/levels, a tether system, a psi monitoring sensor, a magnetic closure system(s), a plastic or other material, such as polystyrene, or such as aircraft aluminum insert that is welded in a PVC film pocket and housed on the exterior of the inflatable bladder that acts in tension, and an inflatable bladder system positioned on at least the neck portion of the gaiter member. The inflatable bladder system works in compression against the wearers neck and vertebrae areas pressing against the wearer's neck, as well as presses against the exterior insert polystyrene or other material that works in tension as a tension wall or cylinder. The bladder sensor system is in constant communication with the App and the health provider, or doctor, designated military personnel system using an App or compatible watch, ring, tablet, cell phone, smart tv, or laptop. When the pressure sensor system senses that there is a change from the predetermined desired psi pressure rating of the bladder system, the actuation system monitors and continually inflates the bladder to achieve and maintain optimal designated pressure through the maintenance pump. In a preferred embodiment, the sensor system including, but not limited to a blood pressure measuring device, $SPO_2$, pulse, heart rate, heart rate variability, prospectively EKG, and also in the preferred embodiment, the sensor system contains a gyro with an algorithm(s) for fall detection. In another embodiment, the sensor system can be configured such that when in the battlefield the medic may deploy a $CO_2$ cartridge to immediately inflate the bladder to the pre-determined desired psi pressure. For the all plastic health and military cervical collar bladder systems the pump motor and the $CO_2$ cartridge respectively along with the battery and any electronics are housed in the detachable inflation housing. The pressure sensor system can be configured such that it senses when pressure in the bladder changes, and the maintenance motor actuation system inflates the bladder to the targeted predetermined psi pressure. The sensor system can also include at least one health sensor, one pressure sensor system, as well as at least one gyro sensor and at least one accelerometer sensor cycling over 800 times per second, at least one Bluetooth sensor, at least one phone system capability, at least one 5 g system, and at least one GPS system.

This invention relates generally to a health and to a military medical cervical collar neck system. Presently, the prior art surrounds hard plastic cervical collars or foam collars, or a combination of plastic intermingled with small air pocket(s). The present invention provides an inflatable health and military medical cervical collar neck supportive system(s) using a PVC film bladder system with an exterior plastic or potentially other materials insert housed in a separate but attached PVC Film exterior pocket in two formats—the first being an all plastic design enabling it to remain on the patient going straight to imaging at the hospital—imaging including, but not limited to CT Scans, x-rays, and MRI's. The second inflatable health and military medical cervical collar neck supportive system(s) real-time tracks and communicates with a doctors key vital bio-metric information using a sensor puck, has a full electronic control system mother board, algorithms designed to maintain desired psi pressure using a maintenance pump, a control board with LED red, yellow and green for go-no-go indicator lights for system readiness and blue LED lights for system charge along with two "system status" buttons for increasing/decreasing the psi pressure and emergency deflate if both buttons are pressed simultaneously all contained on one exterior to the cervical collar system tether, a sensor puck to capture and transmit bio-metric data, a battery, flex and other wiring, Bluetooth, GPS, phone capability, a separate detachable motor contained in the detachable inflation housing that may be charged via the USB port or a wall jack, a two-way port valve that seals the cervical collar bladder, and a magnetized and non-magnetized front closure locking system. Additionally, fall detection and alerts to doctors, etc. are built into the programming, the front closure locking system that is 100% plastic for the CT Scan, or using a magnetic closure support system for the sensor systems that are easily closed and opened by the wearer or the attending doctor/physician/military medic, a tracheotomy opening ready for doctors to insert a trachea tube for breathing when required for the patient. Also the system has flex circuits/ribbons going around to and from all electronics, sensor system, etc connecting the sensor, battery and all electronic systems, and a "manifold assembly" that contains: pressure sensor small maintenance pump, check valve(s), solenoid valve, hose connectors from the detachable pump to the manifold, as well as the back-up pump to and from the manifold system, the manifold hose into the bladder through the valve system, and a quick-release valve. All main electronics will be sewn into the permanent covering that will contain the battery with the main computer board adjacent to the battery, the manifold system, as well as the back-up pump. Regarding the military version, communication while in battle or hostile environments will be designed so as the GPS is not able to be tracked. The system works with existing and loaded software on provided hardware i.e. tablets, phones, and prospectively watches or other devices. The military health collar neck system may or may not have the health sensor system or may have the health sensor with the data captured, but not transmitted in real-time, and may be downloaded at a later time. The health, as well as the military cervical collar neck system(s) are designed to protect and support the human neck post injury to the neck area from base of the skull, or occipital bone down through the cervical vertebrae to the beginning thoracic vertebrae, from the temporal bone to the shoulders and clavicle. This system will not support injuries to the middle of the back or below thoracic 1 into the lumbar vertebrae resulting from accidents that impact the thoracic into lumbar region. The system is designed to support the neck from cervical or C1 down to C7/T1 addressing cervical vertebrae injuries, as well as support the neck for non-skeletal ligament, tendon and soft tissue damage. The system addresses neck support linearly front to back, side to side, diagonally, plus rotationally, providing structure and support fitting snugly to the wearer's neck from the occipital bone in the base of the skull down through the cervical vertebrae, from the ear lobes and temporal bone to the shoulder region and trapezius muscles, from the sternum and clavicle ones to the lower mandible jaw. The health cervical collar bladder system to be used for patient stabilization and transport to the hospital directly to imaging inflates using a detachable motor/pump system inflating with ambient air to fit the wearer's neck using an all plastic port, bladder and closure system. The post imaging sensor system health cervical collar system contains a separate maintenance motor and pump to sustain the desired pressure or psi and total volume with two settings specified per neck circumference size and prescribed by your doctor. Once at the hospital and at the imaging department of the hospital then the motor may be detached immediately before being imaged. The military cervical collar bladder system will also have two versions, and the all plastic version will inflate using a $CO_2$ gas cartridge that will be housed in the detachable and separate inflation housing and will be used to transport to imaging. The post imaging sensor system military cervical collar will inflate using a detachable pump/motor with a maintenance motor to maintain the desired pressure or psi and total volume with two settings specified per neck circumference size and prescribed by the military medic or military doctor, to fit the wearer's neck. The 100% plastic health cervical collar has a detachable pump, battery system for inflation, and the military 100% plastic version has a $CO_2$ cartridge to inflate, also housed in a detachable box. For both health and military cervical collar applications the present invention monitors the wearer remotely and provides the information in real-time directly to your doctor, as well as communicates psi or pressure ratings of the bladder in the cervical collar, key vitals in real-time from the bio-metric sensor arrangement system in which blood pressure, oxygen saturation rate, pulse, pitching/fall detection, EKG, heart rate variability, and more that requires monitoring by the doctor of the wearer while wearing this cervical apparatus support device. Both the health and military system are extremely light weight and flat easily carried by EMT or paramedics for civilians use, and then in the military for medics carrying onto the battlefield, and since the system is already assembled it may be pulled out of the EMT or medics bag, placed around the wearers neck and immediately inflated by the detachable pump for the health version, and for the military version by pulling the tab from the battery releasing the $CO_2$ gas. The 100% plastic are disposable and will have an outer layer of material for comfort. The full sensor system collars will also have an outer washable layer of material with and inner permanent liner system where all electronic systems including the manifold, mother board, all electronics, the battery, and more, as well as there will be an inside bracket at the wearers neck/skin at the carotid artery either left or right side that will house the puck/sensor to read the wearer's vitals. The health cervical collar inflatable neck supportive system will also have a washable fully exterior wicking material that may be removed and cleaned and reused in the sensor system bladder.

In accordance with a first aspect of the present invention there is provided a health and military cervical collar system(s) configured to be received on the neck of a wearer that includes a gaiter material exterior member system, that includes a neck portion, a lower mandible portion, a clavicle portion, a sternum portion, a cervical vertebrae into thoracic vertebrae portion, a right and left trapezius portion, and up to the base of the occipital bone portion, an up to the right side and left side temporal bone above the earlobes portion a sensor system or sensor arrangement system that includes at least one gyro sensor, and at least one accelerometer sensor, and at least one health sensor system positioned next to the wearer's neck on the gaiter member, a sewn material housing the cervical collar bladder system, a washable exterior gaiter member using cooling wicking material, or a normal wicking material, or warmer wicking material, a first pump and motor system to inflate the health bladder, a $CO_2$ inert gas canister for the military system, and a second pump maintenance motor system to maintain desired psi pressure for both the health and military bladder system(s), an actuation system in electrical communication with the sensor system, at least one battery system, a Bluetooth system, a GPS system, a voice communication system, a mother and daughter boards, wires, flex circuits, LED indicator lights for battery charge, LED indicator lights for go-no-go readiness, and whether or not the system is locked and ready for inflation/achieving the targeted desired psi inflation volumes/levels, a tether system, a psi monitoring sensor, a magnetic locking/clip/snap closure system, a plastic or other material, such as polystyrene, or such as aircraft aluminum insert that is welded in a PVC film pocket and housed on the exterior of the inflatable bladder that acts in tension, and a inflatable bladder positioned on at least the neck portion of the gaiter member. The inflatable bladder system works in compression against the wearers neck and vertebrae areas pressing against the wearer's neck as well as presses against the exterior insert that works in tension. The bladder sensor system is in constant communication with the health provider, or doctor, designated military personnel system using a compatible watch, ring, tablet, cell phone, smart tv, or laptop. When the pressure sensor system senses that there is a change from the predetermined desired psi pressure rating of the bladder system, the actuation system monitors and continually inflates the bladder to achieve and maintain optimal designated pressure through the maintenance pump. In a preferred embodiment, the sensor system including, but not limited to a blood pressure measuring device, SPO2, pulse, heart rate, heart rate variability, prospectively EKG, and also in the preferred embodiment, the sensor system contains a gyro with an algorithm(s) for fall detection. In another embodiment, the sensor system can be configured such that when in the battlefield the medic may deploy a $CO_2$ cartridge to immediately inflate the bladder to the pre-determined desired psi pressure. For the all plastic health and military cervical collar bladder systems the pump motor and the $CO_2$ cartridge respectively along with the battery and any electronics are housed in the detachable inflation housing. The pressure sensor system can be configured such that it senses when pressure in the bladder changes, and the maintenance motor actuation system inflates the bladder to the targeted pre-determined psi pressure. The sensor system can also include at least one health sensor, one pressure sensor system, as well as at least one gyro sensor and at least one accelerometer sensor cycling over 800 times per second, at least one Bluetooth sensor, at least one phone system capability, and at least one GPS system.

In a preferred embodiment, the sensor system includes one or more sensors including a body sensor in communication with the gyro sensor(s), the accelerometer sensor(s), the psi pressure maintenance sensor(s), system readiness sensor, and the biometric sensor(s). The sensor(s) system can include other sensors (or the sensors can all be included in a single unit or in more than one unit and unit location) that sense directional changes, acceleration/deceleration changes, g-force changes, impact force changes, pressure/inflation, or psi in the bladder changes, biometric changes, and more. For example, the system can include a biometric sensor(s) that monitors or senses heart rate (resting heart rate, current heart rate, hear rate variability), blood pressure, blood oxygenation saturation level (SPO2), step count, EKG, fall detection, and more. The health and military cervical collar system can also include GPS with phone and location capability, and real-time data transmission (e.g., via Bluetooth) through software and information transmitted and available to doctors, and an app on a mobile device, tablet, or other, and the ability to call over cellular, satellite or other networks should the wearer desire, or require assistance. The system also comes with the available software and hardware with an app for data collection and monitoring. The sensor system with a single type of sensor(s) or multiple sensors working together is configured to determine or sense predetermined inflation changes, changes in biometrics, directional changes for fall detection that the doctor would be able to track real-time emanating from the wearer when wearing the health and medical cervical collar neck system. This is communicated via the real-time communication using an app system in a watch, phone, tablet, laptop, etc. to the wearer's doctor or medic. In a preferred embodiment, the neck portion of the bladder consists of a single bladder specifically shaped to fit around the wearers neck with an insert of plastic or aluminum or other material welded to the exterior of the inflatable bladder, one or more layers. In a preferred embodiment the single bladder in PVC Film, or other materials fits the wearer snugly to the wearer's neck from the occipital bone in the base of the skull down through the cervical vertebrae to thoracic 1 or T1, from the ear lobes and temporal bone to the shoulder region and trapezius muscles, from the sternum and clavicle ones to the lower mandible jaw. In particular, the neck portion can include a single bladder. In a preferred embodiment the inflatable bladder is directly connected to the exterior PVC Film pocket that houses an insert of polystyrene or other materials that is connected/welded to the exterior of the inflatable bladder with ports so the flow of ambient air for the health bladder or $CO_2$ gas, or another gas, such as Nitrogen, or "N," or Argon, or "Ar" as other examples of inert gases for the medical bladder are used for inflation from either a single or more than one port entry for air or gas insertion. In a preferred embodiment the entire bladder system is an individual or a singular bladder system. In a preferred embodiment the entire bladder system is inflated through at least a single port, but may be fabricated with one or more ports. In a preferred embodiment and contained within the manifold system may be a quick connect/disconnect connector. This connector may include an oval male side with one or more radial "pogo" pins and gas/fluid fill tube, and a female receptor with matching slot(s). Locking clamp wings keep the two parts locked together when the male and female parts are mated together. When the two parts are mated together the pogo pins on one half of the connector contact a pad or pin on the other half of the connector permitting electrical signals to pass through the connector. When the two parts are mated together, a gas/fluid filled tube on one half of the connector may be inserted into a cavity on the other half of the connector and a pressure seal will be formed by an o-ring or gasket. When the two parts are mated together, two locking clamp wings located on one half of the connector latch on to slots/ledges on the other half of the connector. Each clamp wings will have a hook that mate with the slots/ledges on the other half of the connectors. Springs are used to lock and hold the clamp wings in place when the two parts of the connector are mated together. To disconnect the two halves of the connector, the clamp wings are pinched together releasing the hooks from the slots/ledges permitting the connect/connection to be pulled apart. This connector is used to attach and lock the three to four foot in length, which may be shorter or longer, hose emanating from the primary pump or $CO_2$ canister used to initially inflate the health cervical collar. In the preferred embodiment, the quick disconnect connector will be located at the side of the neck to make it easy for the wearer to detach once the cervical collar is fully inflated.

In the preferred embodiment, the sensor system is switched from a deactivated mode to an activated mode when the psi sensor senses a predetermined factor indicating that the health and military cervical collar system is fully locked, activated and inflated and is being worn by the wearer. First the separate biometrics health sensor must be in contact with the user's skin or other sensing facto near or over the carotid artery on either side of the wearer's neck, and is activated once the system is properly closed with LED indicator lights showing the system is ready or "go" and is ready to sense, transmit and store data. In a preferred embodiment, the health sensor is positioned to contact the wearer's skin near the carotid artery or other artery available in the neck and clavicle area.

In a preferred embodiment, the cervical collar system includes a bladder airbag system that is deployed in the health system using a detachable portable pump motor used to inflate the bladder also with a secondary maintenance pump motor to sustain, as well as may be used with the detachable pump for initial inflation, the desired psi inflation pressure, which is built into the cervical collar bladder system. The health cervical collar health sensor arrangement using a real-time constant communication system mechanism to capture and transmit health data, and an inflation connected bladder system, resulting in inflation using atmospheric air for the health bladder and $CO_2$ gas canister for the military option to inflate the bladder system to a pre-set desired psi inflation pressure. The health pump in the inflation housing is then detached and the second pump maintenance motor using a battery system will maintain the desired pressure rating in the bladder system, which is held in an interior pocket of the cervical collar system resulting in sustained to set psi aspiration of the inflatable health bladder cervical collar. The current invention also includes in both the health as well as the military cervical collar system breathable latex-free single or double knit fabric sewn over the bladder system, as well as a washable gaiter worn over the neck for the health bladder, a sensor arrangement in the form of a digital gyroscope arranged with specific characteristics surrounding the wearers positioning, a gas canister actuation mechanism for the military option and an on/off port for pump motor for the health option, and an inflation tube, a triggering mechanism, a compressed $CO_2$ gas cartridge, a sensor to engage the digital gyroscope, and an inflatable cervical collar system. In another embodiment the system can communicate via Bluetooth. In another embodiment the system may communicate using GPS, or another approved system for the military. The sensor system can communicate with the actuation system via a wired or a 5 g wireless (e.g., Bluetooth) connection.

In a preferred embodiment, the method includes cervical collar bladder airbag system that is deployed by the military medical personnel using the attached $CO_2$ gas inflation device using a pull-tab trigger mechanism on the battery or on the electronic display system of the detachable inflation housing. The trigger mechanism then releases the $CO_2$ compressed gas from the cartridge through the actuation mechanism held in an interior pocket of the military cervical collar resulting in aspiration of the inflatable safety bladder protection collar.

The military method also embodies a second pump motor system with a psi pressure sensor that will maintain the desired psi pressure rating in the bladder system. The second pump motor that is contained a material pocket of the cervical collar system resulting in maintenance of the desired aspiration pressure of the inflatable cervical collar. In another embodiment the system can communicate via Bluetooth.

The system of the present invention may contain both the digital gyroscope(s), one or more accelerometers, as well as the bio-metric sensor that leads in tracking, monitoring and disseminating the health data via Bluetooth, GPS or 5 g to the doctor monitoring the wearer. The system may also include sensors to engage the digital gyroscope, so the digital gyroscope recognizes when it is not being worn—the digital gyroscope for fall detection will activate once it is on the wearer's body and will disengage if not deployed once taken off the wearer's body.

The invention generally relates to health cervical collars used post-operative, post accidents for the neck in the forms of cervical collars, traction collars, first response collars, cervical orthosis, low density packs, and foam collars.

Additionally, neck injury is as important as head injury and typically is in relationship to head incidents. Concussions may occur and neck injury may occur from impacts, acceleration, deceleration, side to side whiplash, angular whiplash, and more. Support of the neck with concussions also assists in the overall healing process.

It is desirable to support the neck, as noted above the neck is an important aspect of protecting the head and brain from further damage, whether it is tissue only, or cervical breaks, or cartilage damage, or all of the above. Typical protocol for EMT's is to place the cervical collar on the wearer as well as place the injured on a backboard for transport to the hospital.

The developing brain may indeed be more prone to injury than an adult, mature brain because neurons are growing faster and connections are still being made. There is not the redundancy that there is in an adult brain." In addition, "younger children have proportionately bigger heads than adults, and weak necks, so the ability to property support the neck is critical post injury. A blow of the same degree exerts more acceleration force to a child (particularly under the age of 12 or so) than to an adult, because of the relative weakness of the neck musculature, which essentially acts as a shock absorber. Diffuse cerebral swelling is another serious condition that may be found in the child or adolescent athlete or other accidents. This may also explain why female athletes seem to be more susceptible to concussive injuries than men whose necks tend to be stronger. Additionally, children's brains take longer to recover, and concussive symptoms do not show up immediately or within a couple of months like adults, and actually may show up years down the road post trauma.

While it is the desire and goal that a cervical collar, and other types of cervical neck devices are used to support the wearer's neck post injury, it should be noted that as to the health and military cervical collar of the present invention, due to the nature of the shape and variability of sizes of necks and shapes circumference, height, depth, radius, etc. can completely, totally support 100%, or prevent further injuries to those individuals wearing the collar.

Cervical collars have been used for decades, and the embodiment of the present invention is such that greater continuity of support for all the variability of neck sizes may be better supported. In addition, biometrics may be tracked real-time, data transmitted also in real-time to the doctor, maintenance of the desired psi pressure may also be maintained without the need of the wearer to adjust, and finally the military option provides the medics on the battle field with a ready device that is flat, lightweight, easily transported and easily inflated in the midst of battle or conflict where time and safety of the war fighters and the medics are under intense pressure.

An articulating neck post trauma cervical collar neck device for protection post impact and non-impact based injuries, especially relating to motorized vehicle accidents, and all other accidents that have resulting head and neck injury is provided by a bladder system contained within an exterior fabric outer layer or garment containing the PVC Film cervical collar system element garment. an inner inflatable bladder system, an enclosed insert tension wall made of plastic or other materials within a PVC film pocket system welded to the exterior portion of the bladder, and inner permanent enclosed fabric sewn cloth system to house/hold within the following: health monitoring sensor systems, gyros used to detect pitching and falling, etc., psi pressure system(s), control board, mother computer board, manifold, battery, flex or circuit wiring, sensor/puck in a bracket system, a dual front closure system, an opening over the trachea, a two-way port/valve for inflation, a detachable hose and separate pump motor, or $CO_2$ canister, a separate psi pressure maintenance motor, an LED tether or dongle for the wearer to read the readiness capability and battery charge, as well as increase/decrease psi pressure and quick release system, Bluetooth and GPS communication systems, 5 g, a primary pump for the health cervical collar, a primary gas canister release system for the military cervical collar system, a secondary maintenance pump system for both the health and the military cervical collar systems, which are strategically provided in predetermined locations within the layers of the cervical collar system inner garment, plus an outer washable latex-free garment for protecting the human neck and prospectively assisting the head and neck from further injury during the healing process.

The $CO_2$ cartridge military cervical collar actuation mechanism includes a triggering device that can be actuated to open the cartridge by means of a physical trigger contained in the separate inflation housing or actuation system. The inflator punctures the gas canister soft cap releasing the gas filling up the bladder airbag system. The actuation is in response to the medics pulling the release tab from the battery. A compressed gas cartridge is held in the detachable inflation housing. The compressed inert gas cartridge connects to the bladder airbag system through a cartridge actuation mechanism. The actuation mechanism is resultant of the medics inflating the bladder once placed and closed around the wearer's neck.

The digital gyroscope system embodies the ability to sense the wearer's positioning relative to the ground with a pre-set specified degree of angle for fall detection. This digital gyroscope sensor system embodies the ability to sense the wearer's positioning relative to the ground with a pre-set specified degree of angle thereby sending a signal to the doctor or medic notification system mechanism. The digital gyroscope senses body positioning relative to the ground, so any change in positioning past the pre-set degree of angle relative to the ground may immediately notify the doctor or medic that the wearer has fallen. There may be a second sensor lead on the opposite side of the wearer's neck for optimal read from the gyro using pre-set algorithms for fall detection. A doctor and/or EMS may be immediately notified of a fall.

The cervical collar system member, in some instances, will exhibit a layered configuration that includes a soft comfortable washable outer exterior layer of wicking material, an inner exterior latex-free cover, a strong, pliable and durable bladder system (formed out of PVC film, or other materials such as and including, but not limited to thermoplastics including polyethylene, polypropylene, polystyrene, polyvinyl chloride, PVC Film, and polytetrafluoroethylene), a digital gyroscope, accelerometer(s), a Bluetooth system, a GPS system, 5 g, a multiple flex wires, circuits, lead(s) system attached and originating from the electronic mother and daughter boards, a manifold, a solenoid valve system, the voltage battery, the psi pressure sensor system, the LED indicator light system, the magnetic snap locking system, the biometric health sensor system, the hose to attach the health cervical collar system to attach the external air pump, or $CO_2$ cartridge to the cervical collar with a two-way valve/port on the bladder, the military cervical collar system with the inert gas canister system and port with on/off switch. Suitable flexible yet resilient plastics used for the bladder airbag system using polyethylene, polypropylene, polystyrene, polyvinyl chloride, PVC Film (polyvinyl chloride film), and polytetrafluoroethylene that is flexible, but durable for holding shape under impact conditions, transport conditions, durable in imaging processes, excessive heat conditions, not losing its strength or shape. The inert gas cartridge system may have a cylinder shape and consist of, but not be limited to metals, plastics, screws, nozzles, seals, clamps, and other components, parts and materials not listed that are contained within the detachable inflation housing. The maintenance air pump system may have a flat, rectangular, or cylinder shape and consist of, but not limited to metals, plastics, screws, nozzles, seals, clamps, and other component parts, and materials not listed. The bladder airbag system, digital gyroscope, digital gyroscope activation sensing mechanism, electronic sensor system, leads, inert compressed gas cartridge, pump systems, and more in the health and military cervical collar systems may be joined to one another in various different methods, such as mechanical connectors, laser sealed, heat sealed through a variety of methods, stitching or sewing, adhesives, cements, glues, fusing techniques, and other materials or techniques not listed, as well may connect remotely using GPS, 5 g, or Bluetooth.

The current invention is a wearable system with all electronics, or disposable health and military cervical collar technology system that is 100% plastic and able to remain on the patient during transport and go straight into scanning un CT Scans, MRI, x-ray, etc., and apparatus that is designed to support the neck post injury resulting from accidents and injuries. The current invention is designed to support the neck post trauma per a doctor's, paramedics, or medics order(s). The full electronics current invention, may be worn for extended periods of time as the battery will support continuous wear with continuous transmittal of data from 24 hours of non-stop data transmittal, and if programmed for once a minute data transmittal using sleep modes, then it will work continuously for up to one week before recharging is required, and the same all electronics version for the military is a disposable system, or may be a disposable 100% plastic cervical collar for the paramedics and the battlefield for the military. The bladder includes inside the supportive cervical collar in a variety of form(s), such as "inflation bladder," "compression," "insert," "tension," "Bluetooth," "leads," "GPS," "USB port," "5 g," "ability to plug into a wall jack or UBS," "primary separate inflation pump/motor," "secondary maintenance psi pump/motor," "inert $CO_2$ or other gas canister" "sensor(s)/puck," "gyro(s)," "accelerometer," "triggering, or actuation mechanism," "aspirated," "bladder system," "disposable," and/or "compressed," "electronic mother/control board and daughter board," "manifold," "solenoid valve" "inflation housing," "flex circuits," "wiring," "circuits," tether or dongle," "LED light and readiness system," "rapid inflation release button(s)," "sewn inner exterior cloth system with all electronics sewn into the permanent inner layer with "channels/tunnels" to house some or all of the wiring and tubing that may close using Velcro, zipper, etc., "exterior wicking latex-free material using/Velcro that is washable," and more in any combination or layers as needed in the cervical collar contained within the cervical collar system having an outer surface, an inner surface, a front region, a rear region, and two side regions, and with the cervical collar bladder system from the previous filed issued and provisional patent(s) already noted inside the protective cervical collar system in a variety of combination or layer or layer(s) contained within the cervical collar system having an outer surface, an inner surface, a front region, a rear region, two side regions, and top and bottom apertures.

The current invention further comprises an improved reinforcement cervical collars system for the neck for use in a variety of post medical surgeries and post traumas using an insert to support tension, and the bladder designed for compression against the wearer's neck and against the insert in tension. In one embodiment, encompasses a health cervical collar and sensor system designed to address the wearer having a compression system that supports the neck of all sizes with no gaps as seen with the hard plastic cervical collars, as well as support well beyond current available products using soft foam collars. When the head and neck are compromised, as stated herein and articulated from accidents post trauma requires structural support of the neck for soft tissue as well as for compromised cervical vertebrae whether surgery has occurred or not, and healing requires consistent support of the neck in all positions with no gaps. Some medical articles describe how deleterious the hard-cervical collars may be exasperating the injury or trauma. The aspirated neck safety gaiter device(s) can be incorporated into a wide variety of advanced safety cervical collars of a variety of sizes and configurations to produce supportive neck advantages.

The present invention consists of methods and apparatus, which can inexpensively and efficiently manufacture cervical collar(s) in high volume with a specifiable range of design of reinforcement(s) having neck protection as needed with nominal weight of the product. Previously unavailable cervical collar support may assist in overall healing performances for the wearer in general.

The following synopsis represents a summary of aspects of the invention to provide a basic understanding of the invention, and the purpose of the invention. This summary is just that to provide an overview of the invention and is not intended to identify all key critical elements of the invention, or to define/describe the scope, capacity or opportunity of the invention. The summary simply provides some concepts of the invention in a general form, as an introduction to the comprehensive description outlined below.

Aspects of the invention pertain to cervical collar neck members and neck receiving devices, such as a health and military cervical collar system, which includes a neck member, which is engaged as one complete unit, engaged as a double layered (inner and exterior layers) moisture wicking system. The cervical collar system neck member(s) may include a soft comfortable exterior latex-free layer of cooling or warm wicking material, a strong, pliable and durable bladder system (formed out of PVC film or some polymer, such as flexible plastic, including, but not limited to thermoplastics including polyethylene, polypropylene, polystyrene, polyvinyl chloride, PVC Film, and polytetrafluoroethylene), a digital gyroscope, accelerometer(s), a Bluetooth system, a GPS system, a 5 g system, a multiple lead(s)/flex wires, circuits system attached and originating from the electronic mother/control and daughter boards, the voltage battery, the psi pressure sensor system, the LED indicator light system, the magnetic snap locking system, the biometric health sensor system, the hose to attach the health cervical collar system to attach the external air pump or $CO_2$ for the military system to the cervical collar with a two-way port/valve on the bladder, the military cervical collar system with the inert gas canister system and port with two-way close/open, on/off switch, held in the detachable and separate inflation housing. The 100% plastic system elements above with exception of the main inflation motor or $CO_2$ cartridge and the battery are contained within the wicking cervical collar system inner member. The inflation port/valve allows interchangeability. Suitable flexible yet resilient plastics used for the bladder airbag system using polyethylene, polypropylene, polystyrene, polyvinyl chloride, PVC Film (polyvinyl chloride film), and polytetrafluoroethylene that is flexible, but durable for holding shape under impact conditions, laying on the bladder, excessive heat conditions, not losing its strength or shape. The inert gas cartridge system may have a cylinder shape and consist of, but not be limited to metals, plastics, screws, nozzles, seals, clamps, and other components, parts and materials not listed. The maintenance air pump system may have a flat, rectangular, or cylinder shape and consist of, but not limited to metals, plastics, screws, nozzles, seals, clamps, and other component parts, and materials not listed. The bladder airbag system, digital gyroscope, digital gyroscope activation sensing mechanism, electronic sensor system, leads, inert compressed gas cartridge, pump systems, and more in the health and military cervical collar systems may be joined to one another in various different methods, such as mechanical connectors, laser sealed, heat sealed through a variety of methods, stitching or sewing, adhesives, cements, glues, fusing techniques, and other materials or techniques not listed. Data is stored for up to three days, and battery power may go into dormant mode to preserve battery power awaking at pre-set periods of time to capture/communicate and allow calling using GPS and 5 g. All electronics will have TPU (thermoplastic urethane) housings that are flexible and will be sewn to the inner exterior permanent covering.

Additional aspects of the military invention relate to sample methods for providing cervical collar support system using a cartridge actuation mechanism includes a triggering device that can be actuated to open the cartridge by means of a pull tab releasing the block from the battery in the cartridge solenoid spring loaded inflator actuation system, filling up the bladder airbag system at a preset psi per second fill rate.

In accordance with the present invention embodiment, the apparatus comprises a cervical collar support system in the form of a cervical collar system, and the cervical collar system comprises a sidewall, front-wall, and back-wall, and defines an opening(s) for a head and shoulder areas of a wearer. The layered exterior enclosures(s) of the cervical collar system comprise an exterior separate wicking outer latex-free fabric layer, and a more permanent inner fabric layer that is exact fit to the inflatable cervical bladder both of which are positioned proximate to the outer fabric layer. The cervical collar system comprises a single bladder with a sidewall(s), a front-wall(s), and a back-wall(s) in the form of a single vertical bladder. The bladder acts as one contiguous unit and defines an opening(s) for a head of a user or wearer. The insert acts as one contiguous unit with a front wall, side walls, and a back wall. The cervical collar system is applied to the wearer in a deflated flat relationship that is then wrapped around the wearer's neck, and once the closure system is locked and activated around the wearer's neck then is inflated into an expanded relationship in support of the wearer's neck injury.

In accordance with another embodiment, the apparatus comprises a cervical collar system having a longitudinal axis. The cervical collar bladder system also comprises a sidewall extending circumferentially about the longitudinal axis. The sidewall comprises an outer wicking stretchable fabric layer, an inner fabric layer, and an inner inflatable bladder with a polystyrene plastic insert that is welded into a pocket and welded to the bladder, but which is wholly separate from the single bladder and is made of polyurethanes, PVC Film, or any polymeric material attached to both the outer and inner stretchable fabric layer(s), where the bladder layer defines a connected cavity, void or pocket(s) receiving device to house or hold the ambient air for the health cervical collar and $CO_2$ inert gas for the military cervical collar when released through the actuation mechanism system. The inner layer also comprises a layer positioned within the outer layer, the inner layer having a full circumference surface, where it is circumferentially spaced in relationship to the outer layer and resides directly around/over/encompasses the inflatable bladder. The bladder has a top edge surface, a bottom edge surface and a circumference sidewall surface to define a cavity, void, pocket there between the inner layer and the outer layer. The insert has a top edge surface, a bottom edge surface and a circumference sidewall surface residing within a defined cavity, void, pocket there between the bladder and the inner layer. The inner layer wicking material has an inner and outer surface a top and bottom surface with electronics sewn into the inner layer to house the related electronics systems. The outer layer system is washable and removable having an inner layer, and outer layer, a top layer and bottom layer and houses the entire cervical collar bladder system using Velcro or a zipper, or button or some other method to close for closure.

In accordance with yet another embodiment, the cervical collar system apparatus is to be worn by a user, or as stand-alone neck support in the form of a cervical collar system to be worn by the users or wearer post head and neck trauma. The cervical collar system comprises a wicking stretchable outer fabric layer, an inner fabric layer, a space in between the inner and outer layers where there is a definition of cavities carved out in the outer layer housing receiving and showing the electronic devices to house the mother and daughter boards, and all other electronics, the battery, the biometric sensor, the gyros, the accelerometers, the expended gas contained within the inert canister until triggered by the actuation mechanism, the secondary motor/pump to maintenance of psi pressure within the bladder system. The stretchable wicking exterior fabric layer(s) are configured to contact and generally snugly conform to the inflated bladder, as well as the neck of a wearer.

In a preferred embodiment, the method includes a system contained in a breathable wicking material, such as sold by Under Armour and others with an outer fabric layer and an inner fabric layer, or closed/sealed bladder made of PCV film, polyurethanes, polyolefins or any polymeric material to receive the ambient air or inert gas once triggered by the actuation mechanism locked within the bladder that is directly inside the inner fabric layer permanently enclosed environment. The present invention also includes in the health and military cervical collar system breathable double fabric knit as the exterior/outer fabric layer and the inner fabric layer that also may include a lead system, and may include a Bluetooth system and may include a GPS system that is also embedded to work within the system.

The method embodies a 100% plastic and disposable health and military cervical collar system technology system and the fully loaded electronic health and sensor system.

The present invention looks at a neck protective device for protection post trauma, accidents and injuries, is provided by a fabric or wicking outer and inner fabric layer(s) material/element/member, or garment, with an inner enclosed plastic or flexible polymer system with a cavity to receive the release of the inert gas contained within the canister housed in a pocket in the cervical collar system located at the base of the back of the neck above the clavicle.

The present invention will have an outer layer attached to the inner layer via at the top and bottom of the cervical collar system, which may be constructed using RF Welding, Sonic Welding, stitching or sewing, sealants or adhesives, heat sealing, cements, glues, fusing techniques, and other materials or techniques not listed, or a combination thereof, and the inner bladder system contained and sealed therein and contained within the inner layer may be constructed using stitching or sewing, sealants or adhesives, heat sealing, RF welding, sonic or ultrasonic welding, cements, glues, fusing techniques, and other materials or techniques not listed, or a combination thereof. The exterior or outer fabric layer, the inner fabric layer, the inner durable plastic bladder layer, lead(s), sensor(s), triggering/actuation mechanism, inert argon gas canister, may be joined to one another in various different methods, such as mechanical connectors, stitching or sewing, adhesives, cements, glues, fusing techniques, and other materials or techniques not listed.

The following description includes various examples of the invention, which are referenced and reference is made to the associated drawings, which form a part hereof, and in which are shown by way of illustration example systems. Also, the following description includes various examples of the invention, which are referenced and reference is made to the associated drawings, which form a part hereof, and in which are shown by way of illustration example environments and usage the invention may be employed. It is to be stated that other configurations, usages, aspects of use, parts, portions, example systems may be used and structural and functional modifications or alterations may be made without taking leave from the scope of the present invention. Terms, such as "around," "through," "top," "bottom," "side," "above," "below," "underneath," "over," "clear," "transparent," "inner," "outer," "coils," "fluids," "soft," "wicking," "single," "double," "force," "impact," "linear," "rotational," "angular," "acceleration," etc. may be used to describe the invention, and the various examples, and example aspects, facets, features, elements of the invention, these terms are used herein as a matter of descriptors and for practicality and expediency based upon the example orientations as shown in the illustrations. Nothing in this specification should be construed as requiring a specific three-dimensional orientation of structures in order to fall within the scope of this invention.

General Description of the advanced safety technology health and military cervical collar system receiving devices according to the invention.

Some aspects of the present invention relate generally to health and military cervical collar systems, to airbag protection devices, to protect the wearer's neck post trauma. The health and military cervical collar system protection technology system fits on a wearer's neck. The electronic sensor system may occupy one or more placements within the base of the neck portion of the health and military cervical collar system. The digital gyroscope may occupy one placement within the cervical collar system. The electronic flex circuits/leads or wire may occupy one or more placements within the neck or clavicle area portion of the health and military cervical collar system. The Bluetooth may occupy one placement within the neck or clavicle area portion of the health and military cervical collar system. The inflatable safety bladder airbag system may occupy one or more placements within the neck portion of the health and military cervical collar system. The insert may occupy one or more placements with the neck portion of the health and military cervical collar. The inert compressed gas canister actuation mechanism may occupy one or more placements within the inflatable housing portion of the health and military cervical collar system. Any of the sensors discussed herein may be placed in one or more areas of the neck portion of the health and military cervical collar system.

The health and military cervical collar system may be formed from a variety of comfortable wicking materials already in use in today's market, and may be formed with a variety of characteristics in the prior art. The electronic sensor/puck arrangement system may be formed from a variety of materials already in use in today's market and may be formed with a variety of characteristics. The bladder airbag system and any components thereof, such as the insert, the actuation mechanism, digital gyroscope and accelerometer(s) mechanisms, the $CO_2$ cartridge, the triggering mechanism may be formed from a variety of materials and may be formed with a variety of characteristics. All additional systems may be formed from a variety of materials already in use and formed with a variety of characteristics including but not limited to: the electronic control/mother/daughter boards, the manifold, the psi pressure sensors, the soft and hardware, the tether or dongle with all LED indicator lights, the detachable hose, the detachable pump, the maintenance pump, the sensor/puck bracket, the closure system, the flex wiring, leads, circuitry, the battery, and more.

The cervical collar system member portion of the cervical collar system contains the electronic sensor arrangement system, including at least one electronic sensor, at least one digital gyroscope, and at least one sensor distributed at the base of the neck portion of the gaiter system and are stitched, or some form of contact to maintain positioning in between the layers of materials of the cervical collar system, but not being limited and may touch the wearers skin on the neck. The digital gyroscope is also located at the base/back of the neck portion of the health and military cervical collar system. The electronic sensor is located at the base/back of the neck member portion of the health and military cervical collar system, or at the side member of the health and military cervical collar system. Additionally, the neck member may include at least one lead or wire extending therefrom the electronic sensor arrangement system. Additionally, the neck member may include a wireless Bluetooth sensor system, a 5 g capability and GPS. When the digital gyroscope, single (or multiple) electronic sensor system, coupled with one single lead or wire (or Bluetooth capability) is inserted, or attached with the best method of attachment, in the cavity between the two layers of wicking material in the cervical collar system member, the protrusions may extend vertically and laterally and/or upward or downward between the two material layers (i.e. the digital gyroscope, impact and other sensors will be as flat as possible, but will have some minor protrusions). The wire(s) or lead(s) will be also located in the cavity between the layers of wicking material in the cervical collar system and neck members, the protrusions may extend vertically and laterally and/or upward or downward between the two material layers (i.e. the lead will be as flat as possible, but will have some minor protrusions). The Bluetooth and sensor system may also be touching the wearers skin. The bladder airbag system and insert system will be also located in the cavity between the layers of wicking material in the cervical collar system members, the protrusions may extend vertically and laterally and/or upward or downward between the two material layers (i.e. the bladder airbag system will be as flat as possible, but will have some minor protrusions.

The electronic sensor actuation system of an example embodiment of the invention may occupy a minor portion of the neck members of the health and military cervical collar system, i.e., less than 25%, at least 5%, or at least 1% of the neck member of the health and military cervical collar system and region or area. The digital gyroscope system of an example embodiment of the invention may occupy a minor portion of the entire neck and clavicle members of the health and military cervical collar system, i.e., at least 10%, or at least 5%, or at least 1% of the neck and clavicle member of the health and military cervical collar system and region or area. The electronic lead or wire systems of an example embodiment of the invention may occupy a minor portion of the entire neck and clavicle members of the health and military cervical collar system, i.e., at least 5%, or at least 1%, of the neck and clavicle member of the health and military cervical collar system and region or area. The bladder airbag and insert system of an example embodiment of the invention may occupy a significant portion of the entire neck and clavicle members of the health and military cervical collar system, i.e., at least 50%, or at least 60%, or at least 70%, or at least 80%, or even at least 90% of the neck and clavicle member of the health and military cervical collar system and region or area. The battery, manifold, tether, sensor bracket, port/valve, control board individual systems of an example embodiment of the invention may occupy a significant portion of the neck and clavicle members of the health and military cervical collar system, i.e., at least 10%, or at least 5%, of the neck and clavicle member of the health and military cervical collar system and region or area. The cartridge actuation mechanism may also further include a trigger mechanism connecting the leads to the cartridge containing the inert compressed gas. The electronic sensor actuation system may also further include connections to a single lead or wire, a digital gyroscope, or a Bluetooth, or a GPS system, 5 g, and sensor system. The electronic sensor actuation system may also further include a method to attach the electronic sensor to the material layers, and which may reside in between the two layers of wicking material of the health and military cervical collar system. The cartridge may also have a method of attaching or connecting beyond being located in a pre-designed, sewn, or constructed pocket to hold the cartridge. The digital gyroscope may also have a method of attaching or connecting beyond being located in a pre-designed detachable inflation housing system, sewn, or constructed pocket to hold the cartridge.

As already described, the one or more protrusions included in the neck member and the clavicle member of the health and military cervical collar system as an example of the embodiment of the invention, all of which may extend laterally, vertically, may have depth, may have height, and may be in three-dimensional form.

Also as noted, the one or more protrusions included in the neck member, as an example of the embodiment of the invention, may include at least a single electronic sensor oriented in between the two layers of wicking material of the health and military cervical collar system, while not visible will be noted due to the protrusions extending vertically, horizontally, having depth, having height and being in three dimensional form.

Also as noted, the one or more protrusions included in the neck member, as an example of the embodiment of the invention, may include a Bluetooth sensor system located next to the wearers skin, or a single wire or lead oriented in between the two layers of wicking material of the health and military cervical collar system, while not visible will be noted due to the protrusions extending vertically, horizontally, having depth, having height and being in three dimensional form.

Also as noted, the one or more protrusions included in the neck member, as an example of the embodiment of the invention, may include a digital gyroscope oriented in between the two layers of wicking material of the health and military cervical collar system, while not visible will be noted due to the protrusions extending vertically, horizontally, having depth, having height and being in three dimensional form.

Also as noted, the one or more protrusions included in the neck member, as an example of the embodiment of the invention, may include sensor(s)/puck oriented in between the two layers of wicking material of the health and military cervical collar system, while not visible will be noted due to the protrusions extending vertically, horizontally, having depth, having height and being in three dimensional form.

Also as noted, the one or more protrusions included in the neck member and the clavicle member, as an example of the embodiment of the invention, may include one or more bladder airbag systems oriented in between the two layers of PVC film material of the health and military cervical collar system, while not visible will be noted due to the protrusions extending vertically, horizontally, having depth, having height and being in three dimensional form.

Also as noted, the one or more protrusions included in the clavicle member, as an example of the embodiment of the invention, may include one or more insert system oriented in between the two layers of PVC film material of the health and military cervical collar system, while not visible will be noted due to the protrusions extending vertically, horizontally, having depth, having height and being in three dimensional form.

The bladder airbag system may be formed of a variety of materials and/or include a variety of features or element to alter or adjust characteristics of the bladder airbag receiving device. For example, the pliable and durable bladder system may be formed out of PVC film, or some polymer, such as flexible plastic, including, but not limited to thermoplastics including polyethylene, polypropylene, polystyrene, polyvinyl chloride, and polytetrafluoroethylene.

The electronic sensor system may be formed of a variety of materials and/or include a variety of features or element to alter or adjust characteristics of the electronic sensor system receiving device.

The $CO_2$ system may be formed of a variety of materials and/or include a variety of features or elements to alter or adjust characteristics of the cartridge actuation system. This may be an off-the shelf cartridge actuation system utilized in other products.

The digital gyroscope actuation system may be formed of a variety of materials and/or include a variety of features or elements to alter or adjust characteristics of the fall detection actuation system.

The flex system leads or wire circuitry system may be formed of a variety of materials and/or include a variety of features or elements to alter or adjust characteristics of the cartridge actuation system.

Example Methods of Providing and Using Aspirated Inflatable Safety Cervical collar system Receiving Device Systems According to Examples of the Invention. Additional aspects of the invention include methods of providing and methods of using health and military cervical collar systems.

For example, to insert the cartridge inflator actuation mechanism system, wherein the cartridge contains compressed inert gas, and wherein the cartridge contains a trigger mechanism; to insert the digital gyroscope or impact crash electronic sensor arrangement including leads distributed/situated throughout the cervical collar system member; the neck member including one or more apertures; to insert the bladder airbag system at least a portion of the health and military cervical collar system may be removed or separated between the two wicking layers of material where each of the noted component parts above will be inserted or in the separate detachable inflation housing system.

To insert the to insert the bladder airbag system into the health and military cervical collar system, at least a portion of the neck and clavicle members of the health and military cervical collar system, may be removed or separated between the wicking layer of material where each of the noted component parts above will be inserted.

To insert the Bluetooth and sensor arrangement system into the health and military cervical collar system, at least a portion of the sensor will be next to and touching the wearers skin in the neck region specifically by the carotid artery.

Specific examples of the invention and the structures according to the examples of the invention are described in greater detail below. The reader of the invention should be aware that these specific examples and structures are set forth simply to illustrate the invention, and they should not be construed as limiting the invention.

Some aspects of the present invention relate generally to neck supportive system post trauma. The bladder airbag system may occupy one or more placements within the cervical collar system portion of the health and military cervical collar system technology system. The bladder airbag system may occupy one or more placements within the cervical collar system. The inner layer or closed/sealed tube made of PVC film or polyurethanes, polyolefins or any polymeric material may occupy one or more placements within the outer breathable and stretchable wicking material layer of the health and military cervical collar system.

The disposable advanced safety cervical collar system technology system may be formed from a variety of comfortable wicking materials already in use in today's market, and may be formed with a variety of characteristics in the prior art.

Example disposable advanced safety cervical collar system technology system. Aspects of the invention relate to safety systems relates to a disposable advanced safety cervical collar system technology system, or a disposable advanced safety cervical collar system technology system means any device that a user places on or over some portion of the human body. The advanced safety cervical collar system technology system receiving device, (i.e. a disposable advanced safety cervical collar system technology system designed to protect the users neck area), which is a disposable advanced safety cervical collar system technology system and apparatus including a health and military cervical collar system with an outer layer and an inner layer, the inner and outer layers including at least a cervical collar system member, at least one member of the cervical collar system member including a digital gyroscope, and at least one member of the cervical collar system member including a sensor arrangement, and at least one member of the cervical collar system member including a lead or wire arrangement, and at least one member of the cervical collar system member including a Bluetooth arrangement and at least one member of the cervical collar system member, and at least one member of the cervical collar system member including a bladder air bag arrangement, and at least one member of the cervical collar system member including a cartridge actuation mechanism and inert gas canister arrangement.

Example methods of providing and using the health and military cervical collar technology system. The health and military cervical collar system receiving device when worn independently, may not present the user or a wearer with an abnormal feeling of fit, lack of comfort, or the like. The health cervical collar system is designed to maintain the wearer's neck in an optimal position natural to human vertebrae design.

Specific examples of the invention. The various figures in the application illustrate examples of a health and military cervical collar technology system apparatus and product. The health and military cervical collar system in the form of a cervical collar system may be used by paramedics, military medics, in hospital use, or at home use as a base shape or design in the examples of the invention.

There may be many modifications to the specifically described structures, systems, and methods of the invention may take place without departing from this invention. As an example, while the invention has been specifically described with respect to specific examples including preferred modes of carrying out the invention, those skilled in the art will appreciate that there may be numerous variations, combinations, and permutations of the above described systems and methods. Furthermore, various specific structural features included in the examples merely represent examples of structural feathers that may be included in some examples of structure according to the invention. Furthermore, with respect to the methods, many variations in the method steps may take place, the steps may be changed in order, various steps or features may be added changes, or omitted, etc., without departing from the invention. Thus, the reader should understand that the spirit and scope of the invention should be construed broadly as set forth in the appended claims.

A health and/or military cervical collar system(s) comprising a bladder member that includes a neck portion, a clavicle portion, a sternum portion, a cervical vertebrae portion, an occipital bone portion, a temporal bone portion, a mandible bone portion, a trachea portion, a bladder member that receives and holds ambient air or $CO_2$ gas, a bladder insert member that includes a neck portion, a clavicle portion, a sternum portion, a cervical vertebrae portion, an occipital bone portion, a temporal bone portion, a mandible bone portion, a trachea portion, an inner and exterior gaiter member(s) that include a neck portion, a clavicle portion, a sternum portion, a cervical vertebrae portion, an occipital bone portion, a temporal bone portion, a mandible bone portion, a trachea portion, wherein the gaiter member is configured to be received and supportive on the neck of a wearer when worn, a sensor system member that includes at least one gyro sensor and accelerometer member(s) positioned on the inner bladder member next to the wearer's carotid artery, an actuation system in electrical communication with the sensor system, a manifold member, a control board member, a battery member, a set of flex or other wiring members, a bracket member, a closure member, an opening over the trachea member, a port/valve member, a detachable pump/motor member in the inflation housing member, a maintenance pump member, a psi pressure sensor monitoring member, a tube/hose member, a tether/dongle member, LED indicator system readiness lights member, algorithm members, a software and hardware members, a rapid deflation member, a sensor system that reads, stores and transmits bio-metric data using Bluetooth, GPS, a phone capability member, an inner cloth latex-free member, an outer exterior wicking layer member, an all or 100% system ready to enter imaging at the hospital member, an electronic system designed to handle these capabilities in the post imaging member at the hospital for cervical collar use while in the hospital post-surgery and in recovery, at home use and more, and the bladder is positioned on and in support of the neck portion of the wearer in compression wherein the inflated bladder leaves no gaps to the area to be protected post trauma.

The health and/or military cervical collar system wherein the sensor system includes at least one accelerometer(s) and/or a gyro(s). The health and/or military cervical collar wherein the removable and/or replaceable sensor system includes a biometric health sensor/puck system. The health and/or military cervical collar system wherein the sensor system includes a biometric health sensor/puck system bracket housing sewn into the inner layer of the inner cloth gaiter system with the sensor having exposure to the wearer's skin. The health and/or military cervical collar system wherein the biometric health sensor is positioned to contact the wearer's carotid artery.) The health and/or military cervical collar system wherein the inner gaiter member includes an inner layer and an outer layer, and wherein all electronics, the battery, the control board, the manifold, the tether system connection, the port/valve connection, all connective wiring, the gyro, the sensor/puck are positioned and sewn in the inner layer with a viewing window in the outer layer of the gaiter system.

The health and/or military cervical collar system wherein the inflation bladder is positioned between the inner and outer layers of the inner cloth gaiter system. The health and/or military cervical collar system wherein the inflation bladder insert is positioned in a pocket on the exterior of the inflation bladder and is in between the inner and outer layers of the inner cloth gaiter system. The health and/or military cervical collar system wherein the port/valve inflation connection to the separate detachable inflation housing system is positioned on or near the clavicle portion of the cervical collar system member. The health and/or military cervical collar system wherein the bladder includes a single inflation chamber extending upwardly from the clavicle and sternum portion to the mandible portion, extending up from the shoulder trapezius muscle portion to the temporal bone portion, extending down from the occipital bone portion down through all 7 Cervical Vertebrae to Thoracic 1 portion. The health and/or military cervical collar system wherein the bladder insert portion includes a single inflation chamber extending upwardly from the clavicle and sternum portion to the mandible portion, extending up from the shoulder trapezius muscle portion to the temporal bone portion, extending down from the occipital bone portion down through all 7 Cervical Vertebrae to Thoracic 1 portion.

The health and/or military cervical collar system with two bladder portions with the first being the inflation bladder system that resides in compression next to the wearer's neck, and the bladder insert portion that resides in a separate pocket welded to the exterior of the inflation bladder portion to house the bladder insert that acts in tension as the exterior of the inflation bladder system. The health and/or military cervical collar system wherein the inflation bladder portion of the bladder is contoured shaped to fit the wearers anatomy from the base of the skull, or occipital bone down the back to Thoracic 1, from the temporal bone to the trapezius muscles and the shoulders, from the mandible bone to the clavicle and sternum, and is contoured with an opening over the trachea area for access and comfort. The health and/or military cervical collar system wherein the bladder inflation system is in electrical communication with the electronics control board and the battery, and is activated using the inflation button(s) on the separate tether/dongle LED and sensor electronic readiness system attached between the tether/dongle LED board and activation system via a flex wire, or leads, and the control board and wherein the control board and battery are positioned between the first and second inner cloth and/or latex free layers. The health and/or military cervical collar system wherein the bladder inflation may be rapidly/emergency deflated suing the inflation button (s) on the separate tether/dongle LED and sensor electronic readiness system.

The health and/or military cervical collar system wherein the battery charge readiness is indicated by four blue LED lights on the separate tether/dongle LED and sensor electronic readiness system. The health and/or military cervical collar system wherein the sensor system readiness is indicated by three colored indicator red, yellow, blue LED lights on the separate tether/dongle LED and sensor electronic readiness system. The health and/or military cervical collar system wherein the bladder inflation may be adjusted to algorithmic pre-set psi total volume amounts. The health and/or military cervical collar system wherein the bladder inflation may be checked by the psi pressure sensor system and the system automatically adjust to maintain pressure using a maintenance motor that is positioned between the first and second inner cloth layers. The health and/or military cervical collar system wherein when the health sensor system senses the wearer's bio-metrics, collects, stores and relays the data in pre-set time formats.

The health and/or military cervical collar system wherein the sensor system includes a Bluetooth sensor. The health and/or military cervical collar system wherein the sensor system transmits the captured and stored data to the system software and hardware. The health and/or military cervical collar system wherein the sensor system includes a GPS sensor. The health and/or military cervical collar system wherein the sensor system includes a phone capability member. The health and/or military cervical collar system wherein the exterior wicking material member is removable and washable. The health and/or military cervical collar system wherein the entire system includes flex circuitry or leads or wires connecting the battery, control board, the manifold, the port/valve, the tether/dongle system readiness, and the phone capability member. The health and/or military cervical collar system wherein the cervical collar inflatable bladder portion and insert portion of the entire cervical collar bladder is contoured shaped to fit the wearer.

The health and/or military cervical collar system wherein the cervical collar inflatable bladder portion closure system snaps shut/snaps together in two independent vertical columns with clip snap closure systems that are above and below the trachea opening and the top closes in opposition, or opposite direction of the bottom. The health and/or military cervical collar system wherein the cervical collar inflatable bladder portion closure system snaps shut/snaps together in two independent vertical columns that are above and below the trachea opening and the top closes in opposition, or opposite direction of the bottom, and wherein each has a release tab/button/latch. The health and/or military cervical collar system wherein the cervical collar inflatable bladder portion closure system snaps shut/snaps together in two independent vertical columns that are above and below the trachea opening, and has a magnetic closure system that ties back to system readiness on the tether/dongle.

The health and military cervical collar bladder inflation bladder system remote and detachable main pump motor will also have a visual display showing/illuminating the red, yellow, green readiness LED indicator lights, the blue LED battery charge indicator light, the two psi pressure readings and buttons for up or down pre-set algorithmic psi pressure settings, and hold both buttons down for rapid deflation.

In a preferred embodiment, the health and military cervical collar system includes a trachea opening in the front of the collar assembly over the wearer's trachea. Paramedic, emergency room doctors, etc. may unlatch the bottom clip while administering the trachea and then reclose the lower clip system. Preferably, the collar assembly includes a pocket weld around the bladder member to secure the bladder member to the wall member and includes opposite ends that include opposite members of a closure system. The cervical collar system preferably includes a detachable air/fluid hose or conduit, and an exterior or second pump assembly. The trim line of the inflation bladder inner exterior may be sewn cloth or latex free cloth material. The collar assembly may include a pocket member to house/hold the manifold, a sensor/puck member, a bracket member to secure the sensor/puck, a port/valve (two-way) or disconnect assembly to connect for inflation of the bladder member with the detachable air hose and inflation housing members, an LED system readiness tether/dongle board member or user interface assembly, an increase/decrease button system for inflation and rapid/emergency deflation by simultaneously pressing both buttons, a three color (red, yellow, green) system readiness LED light panel, a four blue LED light system for battery charge and readiness, a USB or other electrical communication (it will be appreciated that "electrical communication" herein includes both electricity and data communication), a port, a flex circuit connecting the magnetized closure system to the control assembly or board, a sewn pocket to house all wiring/flex circuits. It will be appreciated that when worn the collar assembly may extend from a back of the neck occipital bone through all seven cervical vertebrae members and thoracic one member, a side of the neck member from temporal bone to trapezius and shoulder members, and a front of the neck member from mandible to sternum and clavicle bone members.

The LED system readiness board tether/dongle member or user interface assembly may include an increase/decrease button system for inflation and rapid/emergency deflation by simultaneously pressing both buttons, a three color (red, yellow, green) system readiness LED light panel, a four blue LED light system for battery charge and readiness, a USB Port, a flex circuit connecting the magnetized closure system to the control board or assembly.

The invention also may include a disposable military cervical collar system using a $CO_2$ gas canister housed in the inflation housing as opposed to a pump with a battery.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
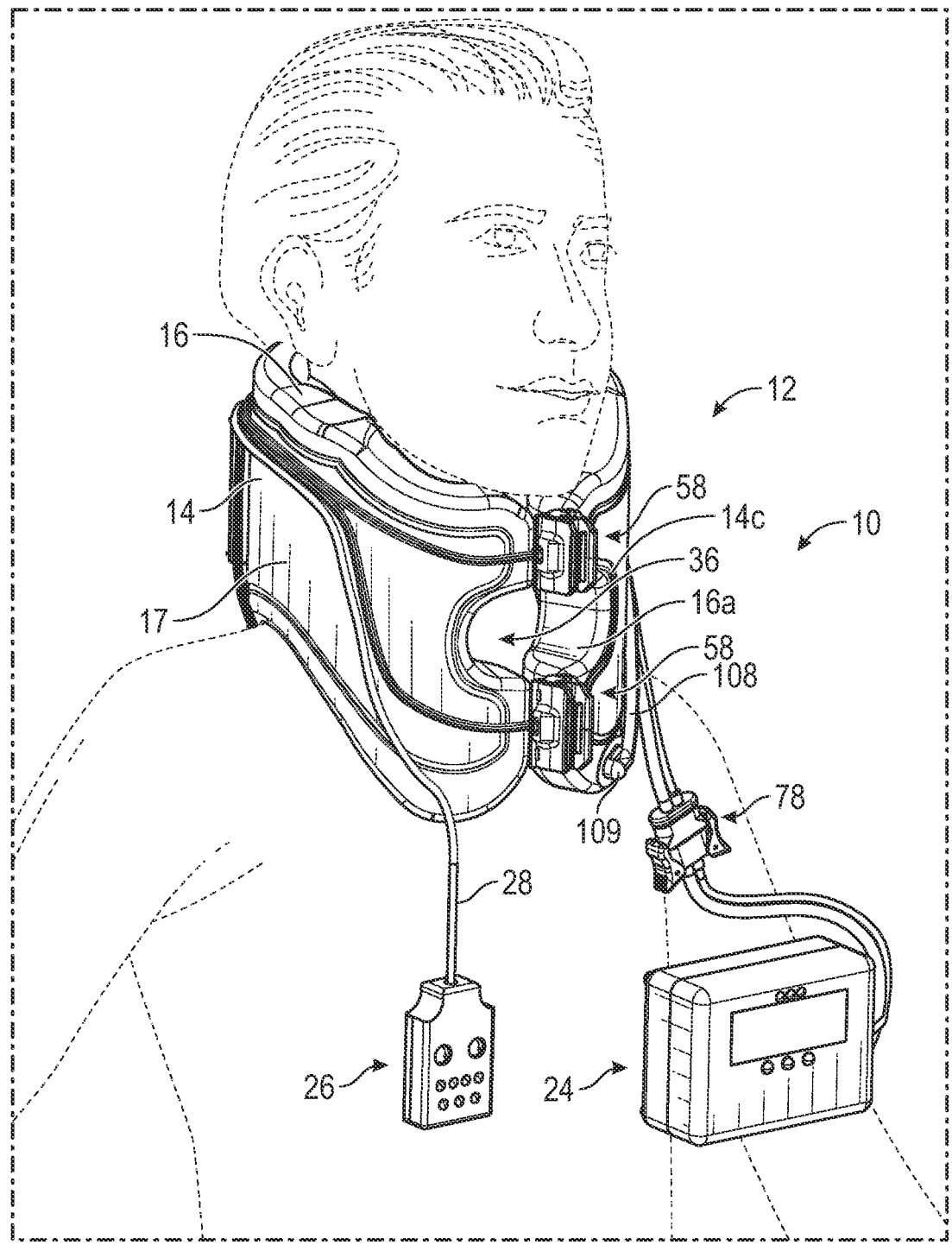
FIG. 1 is a front perspective view of a person wearing a cervical collar system in accordance with a preferred embodiment of the present invention.
Figure 2:
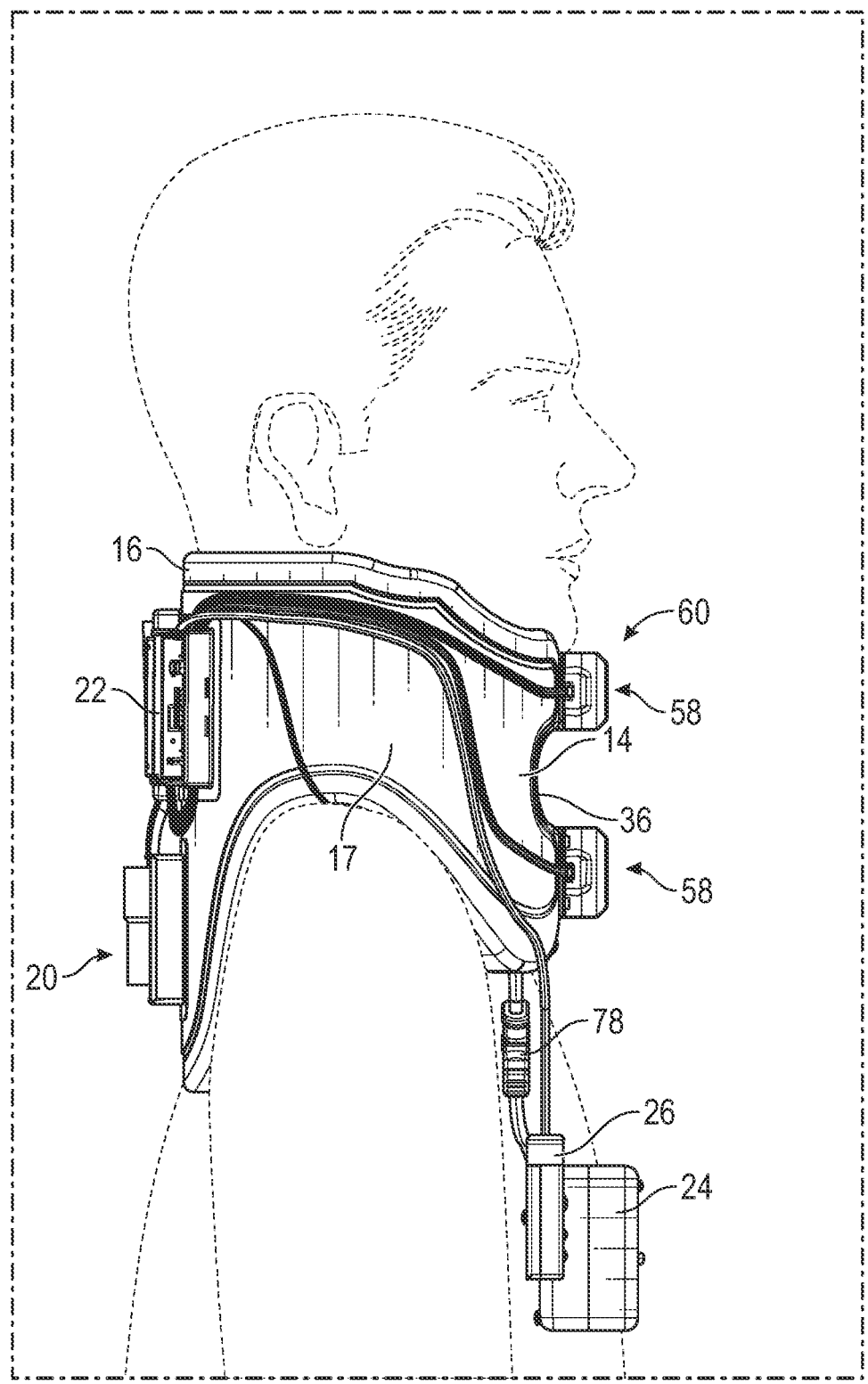
FIG. 2 is a side elevational view of the person wearing the cervical collar system.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, wherein the showings are for purposes of illustrating the present invention and not for purposes of limiting the same, FIGS. 1-12 show a cervical collar system 10 that can be used for protecting a wearer's neck post trauma. As shown in FIGS. 1-4, in a preferred embodiment, the cervical collar system 10 includes a collar assembly 12 that includes a wall member 14 having an inner side 14a and an outer side 14b and a bladder member 16 positioned on the inner side 14a of the wall member 14. The collar assembly 12 includes an open position (FIG. 4) and a closed position (FIG. 1) and is configured to be received on the neck of a wearer. It will be appreciated that FIG. 1 shows the collar assembly 12 in the closed position and with the bladder member inflated. The uninflated position of the bladder member is not shown. It will be appreciated that the The bladder member 16 may be a separate piece where the wall member 14 is welded/attached to the bladder member. In a preferred embodiment, the collar assembly 12 is formed at least in part by folding a piece of plastic (e.g., PVC Film) in one upper location of the bladder member to also include a third overlapping layer with the wall member between the third overlapping layer and one of the folded layers of the bladder member, or two of the layers to form two opposing layers and welding or otherwise securing the three layers to one another (see outer weld line or seam 15 and inner weld line or seem 13 in FIG. 4) and then welding two of the three layers to one another to contain the wall member 14 within the plastic layers. The layers may all begin as two separate pieces of material that are secured to one another as well. The resulting collar assembly includes a semi rigid tension wall member that forms a cylindrical shape when the collar assembly is in the closed position and helps maintain the cylindrical shape when the bladder member 16 is inflated in compression. It will be appreciated that the bladder member 16 and wall member 14 are referred to as a unit herein as the bladder assembly 17.

Figure 4:
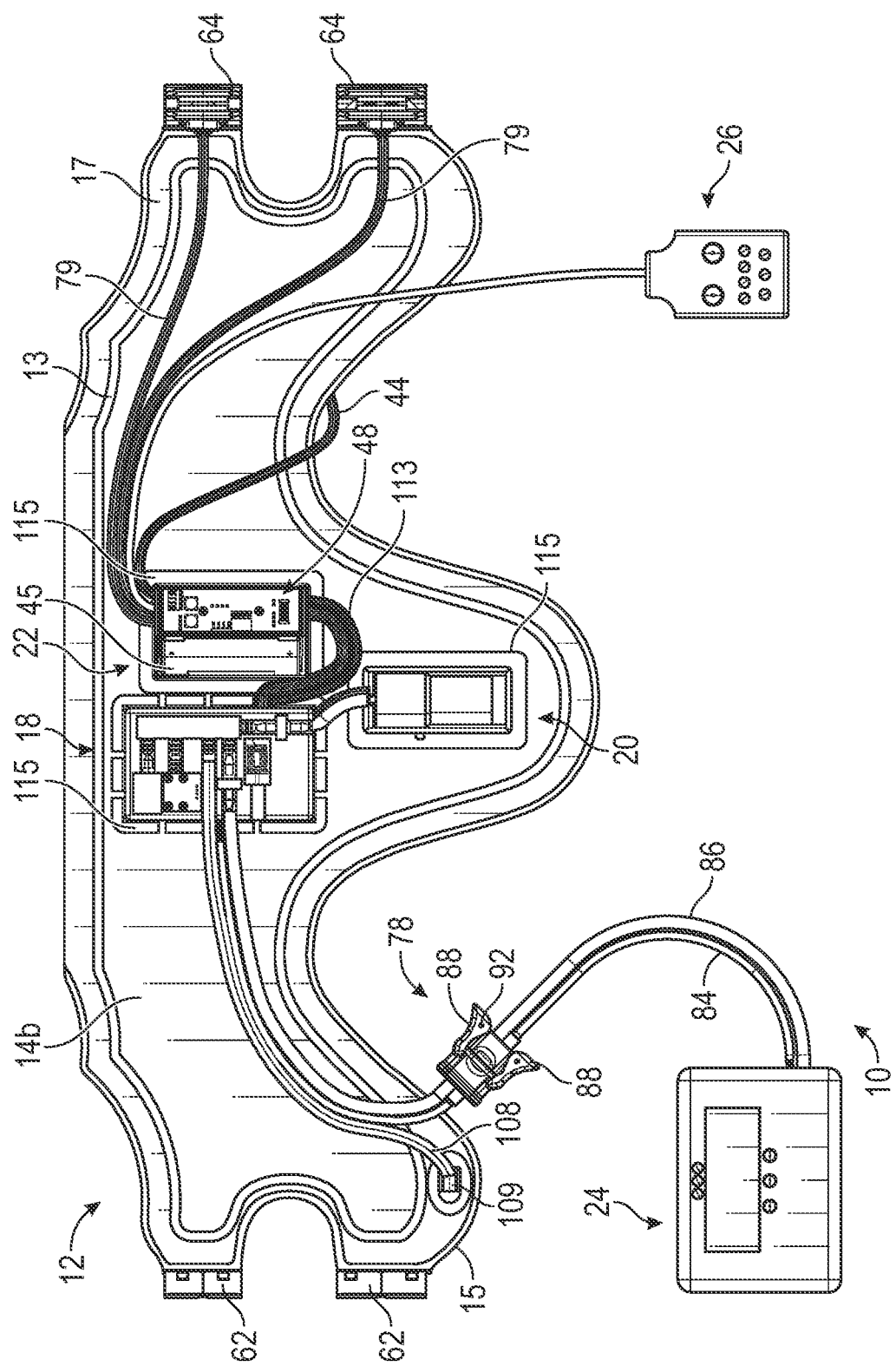
FIG. 4 is a rear elevational view of the cervical collar system in the open position.

As shown in FIG. 4, in a preferred embodiment, the cervical collar system 10 includes an external or first pump assembly 24 that is in fluid communication with the bladder member 16 (which may be through a manifold assembly 18). The cervical collar system 10 may also include the manifold assembly 18 positioned on the outer side of the wall member 14, an auxiliary or second pump assembly 20 positioned on the outer side of the wall member 14 and in fluid communication with the bladder member 16, and a control assembly 22 positioned on the outer side of the wall member 14. Preferably, a user interface assembly 26 is in electrical communication with the control assembly 22. The user interface assembly 26 is preferably external to the collar assembly and is in electrical communication with the control assembly 22 via a cord 28.

Figure 3:
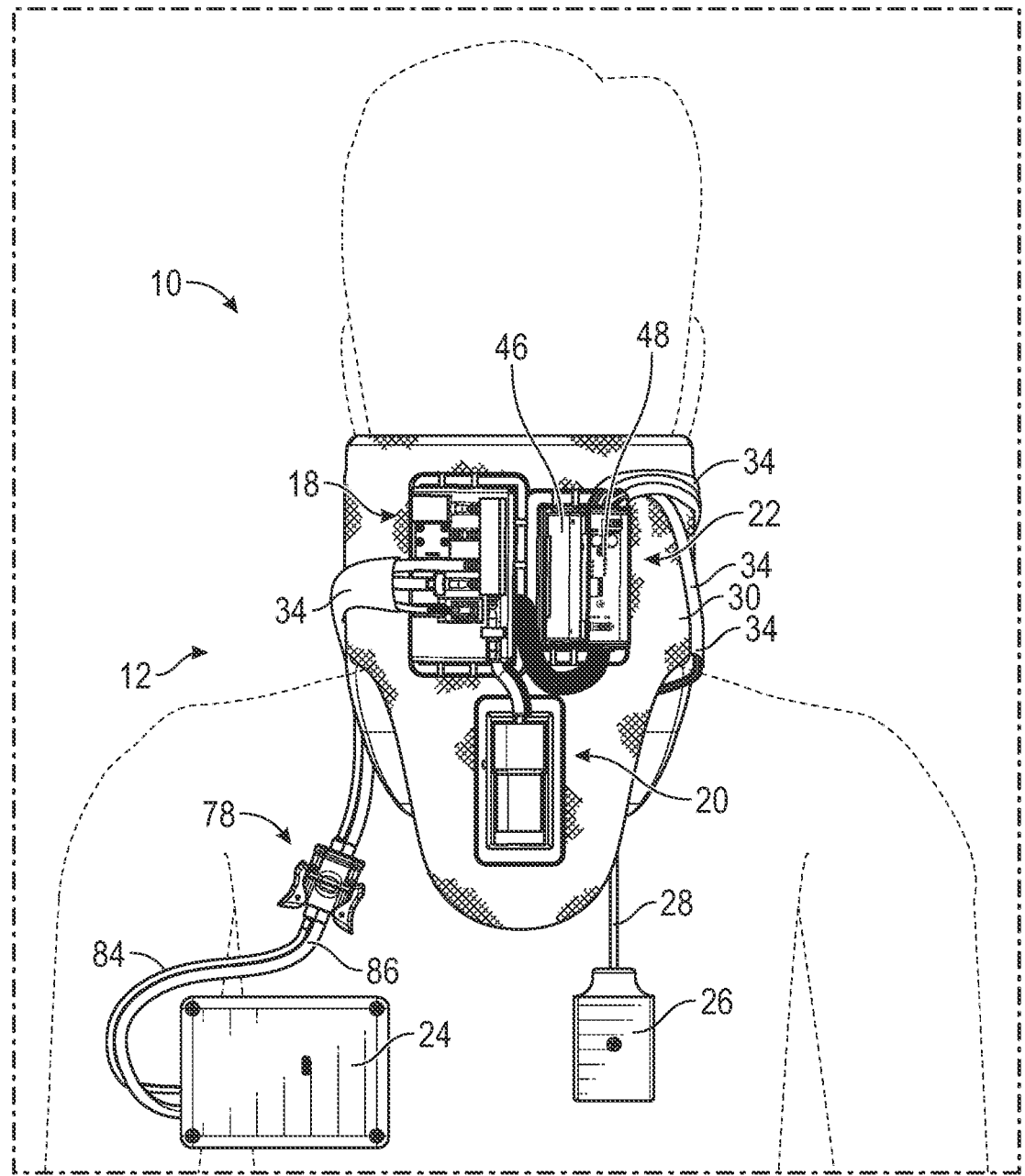
FIG. 3 is a rear elevational view of the person wearing the cervical collar system.
Figure 5:
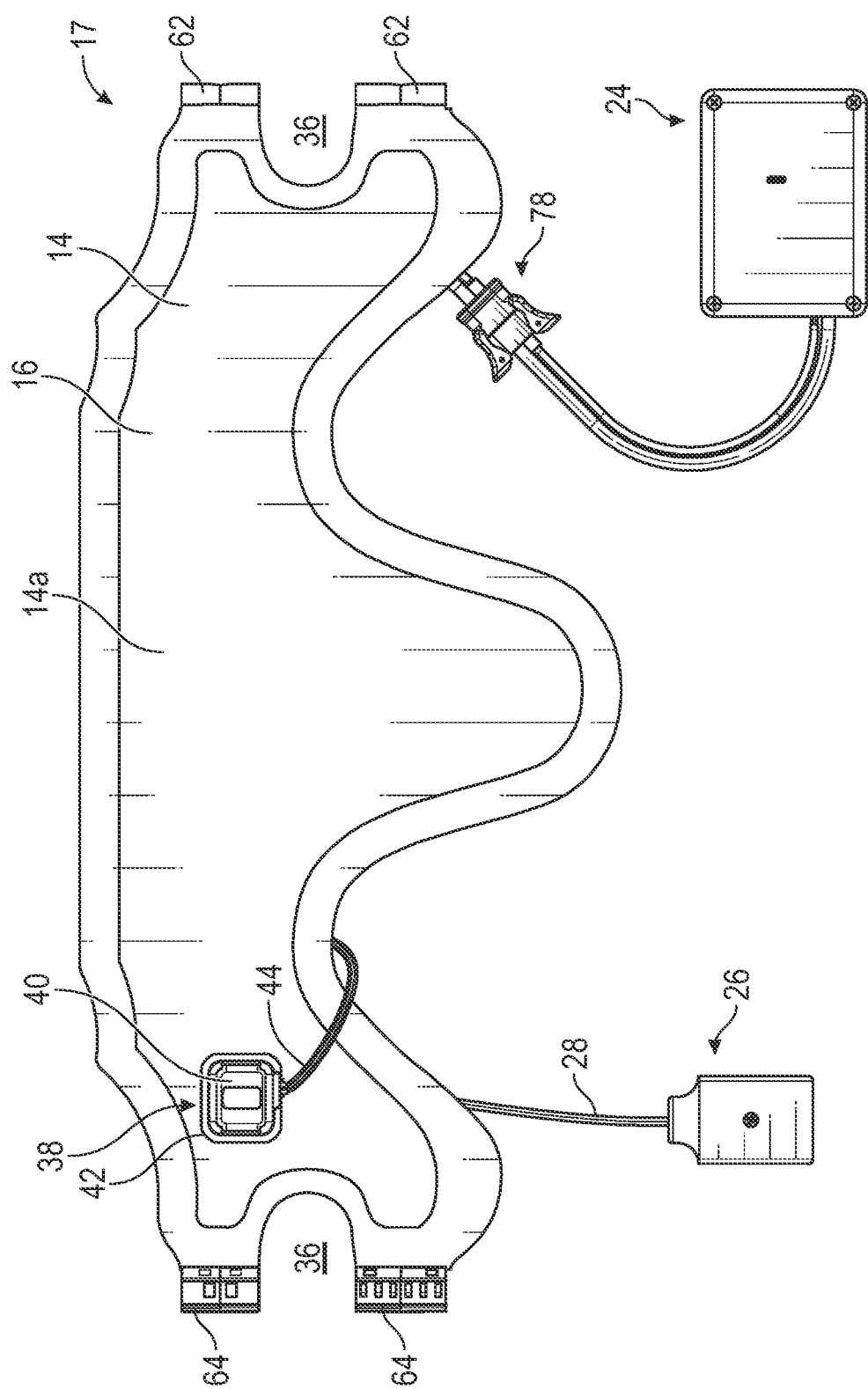
FIG. 5 is a front elevational view of the cervical collar system in the open position.
Figure 6:
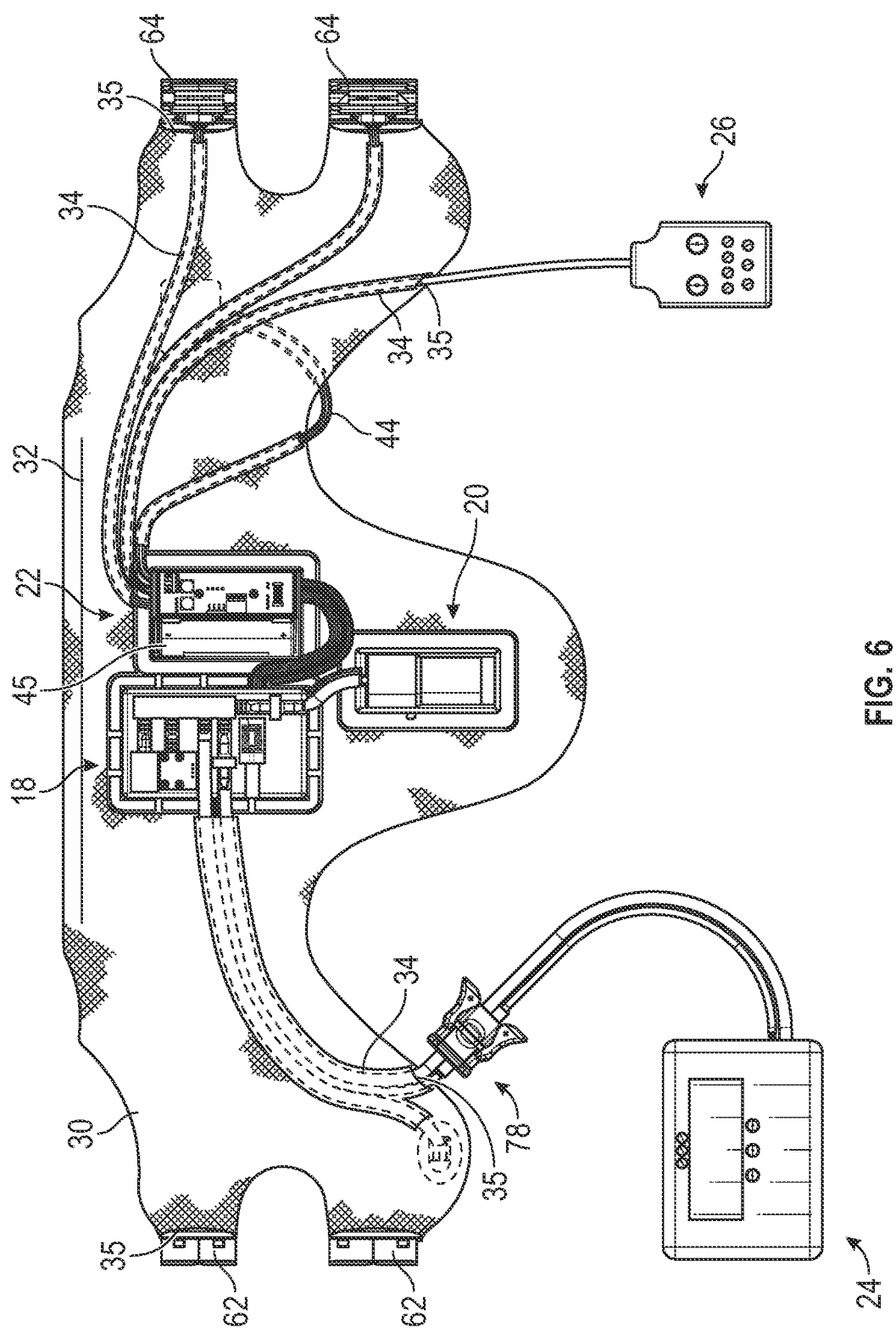
FIG. 6 is a rear elevational view of the cervical collar system in the open position including a liner member.
Figure 7:
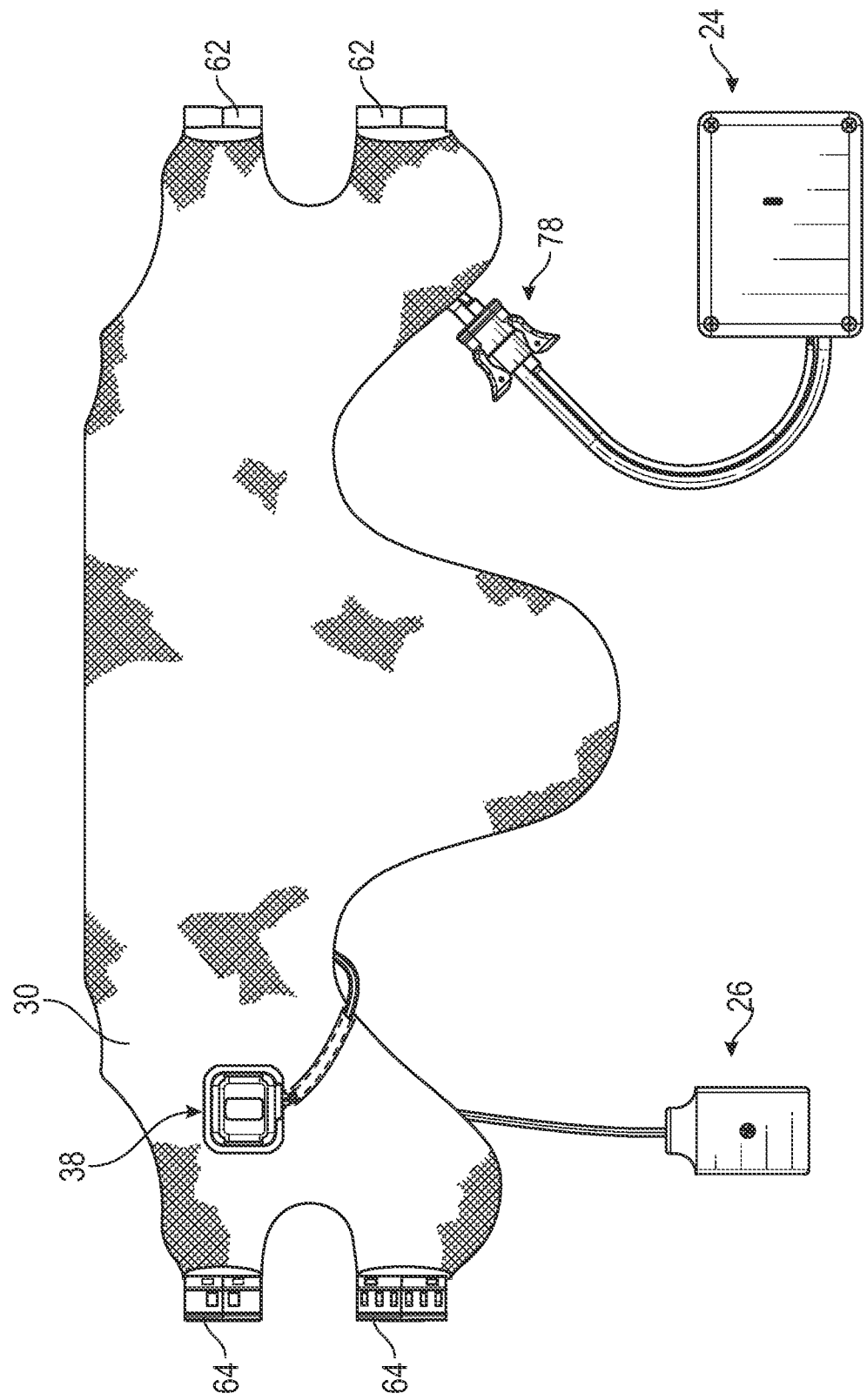
FIG. 7 is a front elevational view of the cervical collar system in the open position including a liner member.

As shown in FIGS. 3, 6-7, in a preferred embodiment, the collar assembly 12 includes a liner member 30 covering the bladder member 16 and wall member 14. The liner member 30 provides a layer or component to which the manifold assembly 18, second pump assembly 20 and control assembly 22 can be secured or attached, for example by stitching. In FIGS. 1, 2 and 4-5 the liner member 30 has been omitted to show the components underneath. In another embodiment, the liner member 30 can be omitted and the manifold assembly 18, second pump assembly 20 and control assembly 22 can be secured directly to the material or layer that covers the wall member 14 or the bladder assembly 17. Preferably, the liner member 30 is made of a fabric material (e.g., latex-free wicking material) and includes an opening 32 through which the components inside thereof can be inserted during manufacture. Opening 32 can be closed by Velcro, a zipper or the like. In a preferred embodiment, the liner member 30 includes a plurality of tunnels 34 through which the various wires and hoses can be routed. Openings 35 can be defined in the liner member 30 or ends of the tunnels 34 so that the barrels 62, clip members 64 and various hoses and wires can extend outside of the liner member 30 (see FIG. 6).

As shown in FIG. 1, the collar assembly 12 preferably forms a trachea opening 36 when it is in the closed position. The wall member 14 and bladder member 16 are formed such that the wall member 14 forms a wall trachea opening 14a when the collar assembly 12 is in the closed position and the bladder member 16 forms a bladder trachea opening 16a when the collar assembly 12 is in the closed position.

As shown in FIGS. 5 and 7, in a preferred embodiment, the collar assembly 12 includes a biometric sensor assembly 38 (also referred to herein as a puck or sensor) positioned on an inner surface of the collar assembly 12 (e.g., on the liner member 30). Preferably the biometric sensor assembly 38 is positioned over the wearer's carotid artery when the cervical collar system is worn. In use, the biometric sensor assembly 38 contacts or is adjacent the user's skin and is activated once the system is properly closed with LED indicator lights showing the system is ready or "go" and is ready to sense, transmit and store data. It will be appreciated, that the biometric sensor assembly 38 can be located in other positions to sense and detect biometric data.

In an exemplary embodiment, the biometric sensor assembly 38 may be removable. For example, the sensor member 40 may be secured within a sensor housing 42 and may be removable therefrom. The sensor member 40 may include any type of technology for taking biometric measurements from the wearer. For example, the sensor member may include LED technology, contact electrodes or other technologies such as are used in biometric sensor systems such as Fit Bits, Whoop straps, EKG's, etc. The sensor member 40 may include a plurality of different sensors and other technologies for taking biometric readings. In another embodiment, the system includes a sensor assembly or sensor member permanently attached to the collar assembly and may not be removable. The biometric sensor assembly 38 may include wires 44 for electrical communication with the control assembly 22 Preferably, the sensor member includes wireless connectivity.

As shown in FIGS. 4 and 6, the control assembly 22 includes a battery 45 and a control board 48, PCB or control member. It will be appreciated that the control board 48 includes all electronics necessary to control the cervical collar system 10. The figures show the wires 44 connecting the control assembly 22 to the biometric sensor assembly. However, these components may communicate wirelessly. Furthermore, the control assembly 22 may include wireless communication (e.g., 5G) to an app on a mobile device, such as a phone or tablet.

Figure 8:
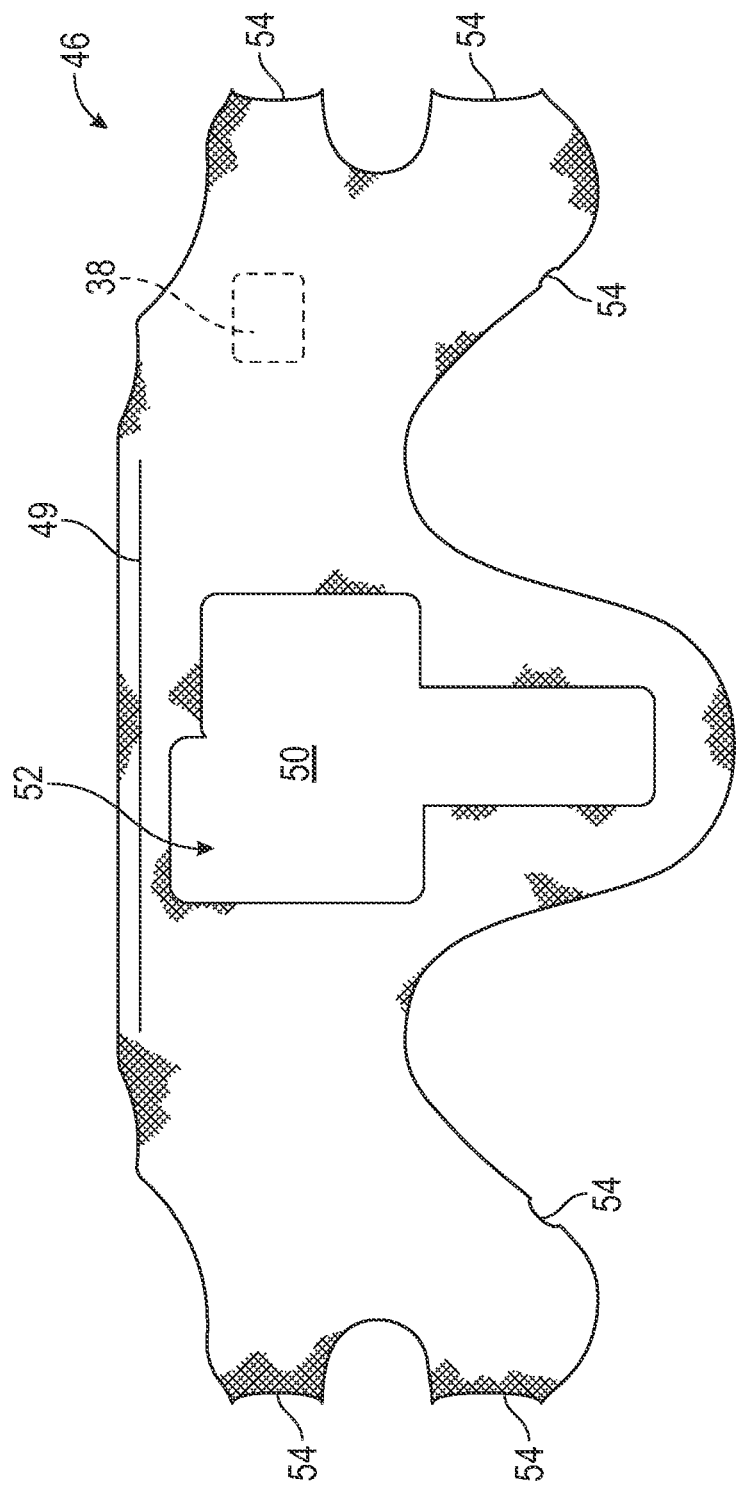
FIG. 8 is a rear elevational view of a sleeve member that can be secured over the collar assembly.

FIG. 8 shows an optional sleeve member 46 that can be used to cover the collar assembly 12. The sleeve member 46 is removable and washable. The collar assembly 12 can be inserted through an opening 49 and into the sleeve interior 50. Preferably, the sleeve member 46 includes one or more housing openings 52 through which the manifold assembly 18, second pump assembly 20 and control assembly 22 protrude. The sleeve member 46 also includes openings 54 through which the clips and various hoses extend/connect. An opening is also included for the biometric sensor assembly 38.

As shown in FIGS. 1-7, in a preferred embodiment, the collar assembly 12 includes one or more, and preferably two, clip assemblies 58, and that together form a or are part of a closure system 60 and that maintain the collar assembly 12 in the closed position. The clip assembly 58 includes a barrel member 62 associated with a first end of the bladder assembly 17 and a clip member 64 associated with the second end of the bladder assembly 17.

Figure 9:
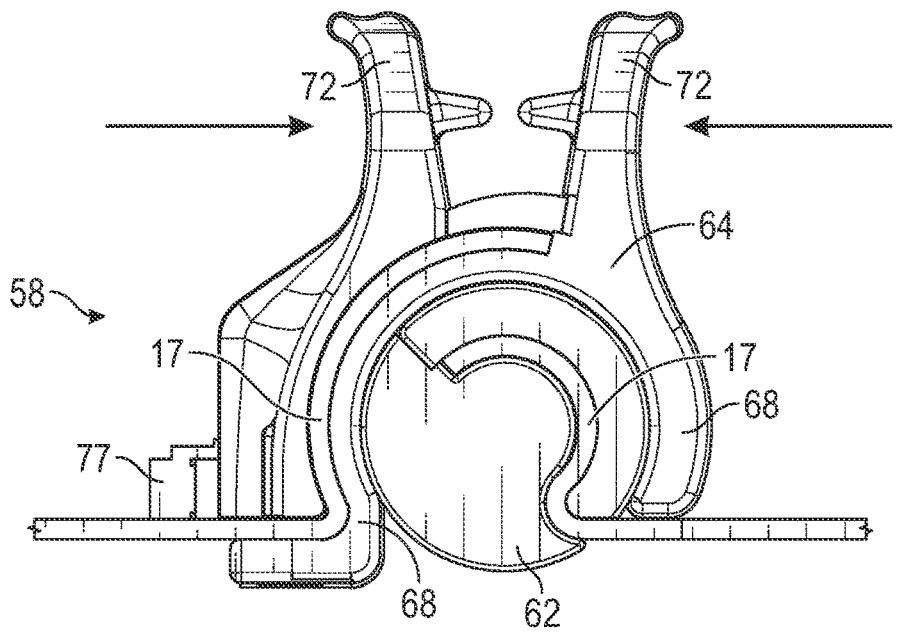
FIG. 9 is an elevational view of the clip assembly in the secured position.
Figure 10:
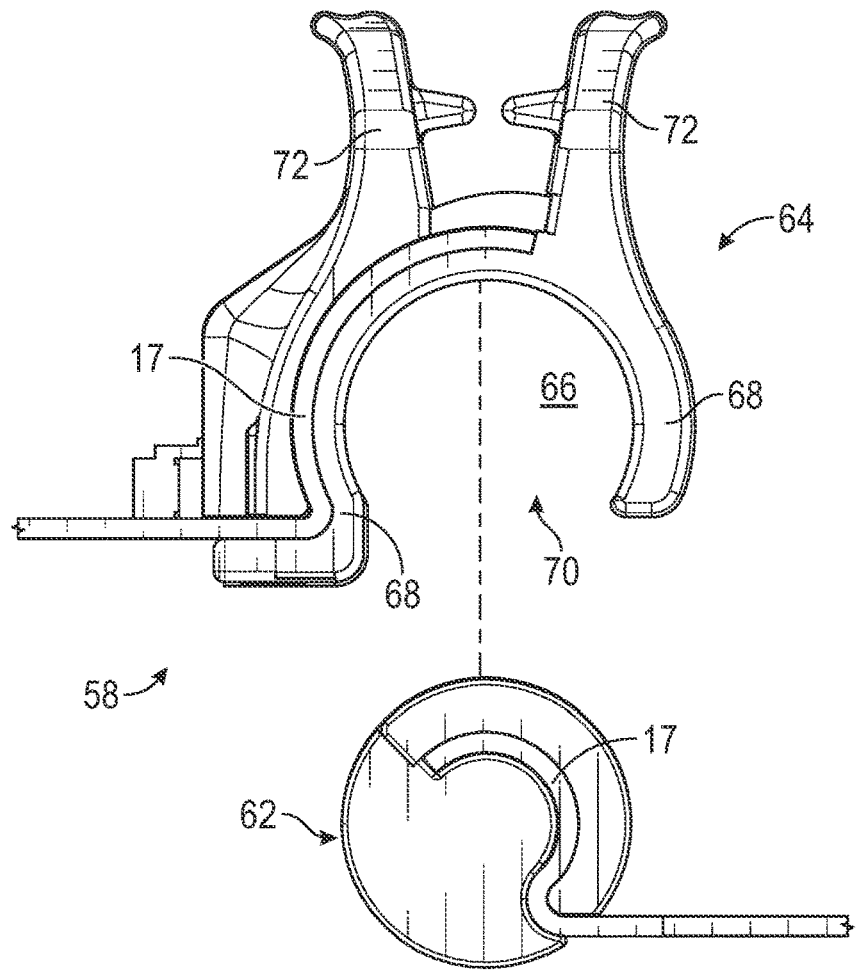
FIG. 10 is an elevational view of the clip assembly in the secured position.
Figure 11:
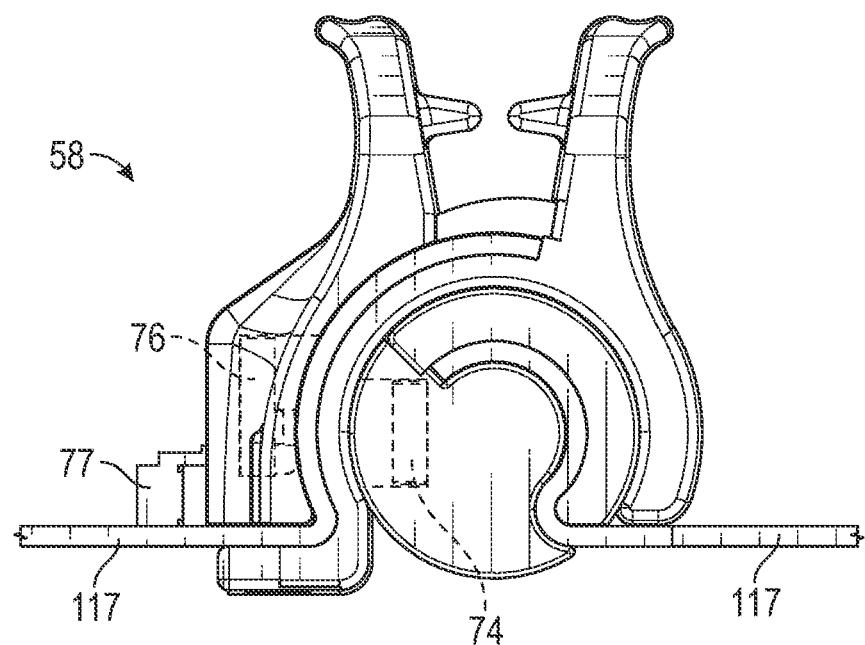
FIG. 11 is a cross-sectional view of the clip assembly.

FIGS. 9-11 show the clip assembly 58 close-up. As shown, the clip member 64 and barrel member 62 each include a portion of the material of the bladder assembly 17 secured therein. It will be appreciated that as a result of the multiple layers or folding during production that is discussed above, that there may be multiple layers (e.g., three layers) of material, such as PVC that forms the portion of the bladder assembly 17 received or secured in the clip member 64 and barrel member 62. These layers are shown as a single layer in the figures. Preferably, the clip member includes a receiving space 66 that is defined by opposing prongs 68. The distal ends of the opposing prongs 68 define a mouth 70 therebetween. Barrel member 62 is sized such that when it is pushed against the distal ends of the opposing prongs 68, the mouth 70 widens thus allowing the barrel member 62 to be received into the receiving space 66. Clip member 64 also includes opposing pincher members 72 that when pinched (see the arrows in FIG. 9) cause the mouth 70 slightly widen such that the barrel member 62 can be pulled out of the receiving space 66. It will be appreciated that the clip member 64 acts as a living hinge, and due to the material thereof, the barrel member 62 can be inserted into and removed from the receiving space 66. It is essentially a snap fit. In another embodiment the clip member 64 may be hinged.

As shown in FIG. 11, in a preferred embodiment, the clip assembly 58 includes a closure sensing system with magnets and/or a Hall effect sensor. As shown, the barrel member 62 includes a first magnet member 74 and the clip member 64 includes a second magnet member 76. The clip assembly 58 is in electrical communication with the control assembly 22. See electrical connection 77 in FIG. 11. Generally, the system will not inflate the bladder if the magnet members are not in proper or predetermined alignment or positioning (and showing a go or no-go on the LED's of the user interface assembly). In other words, if the wearer or user attempts to inflate the bladder, but the clip assemblies 58 are not properly closed the control assembly 22 will not signal inflation of the bladder member 16. Preferably, the closure system 60 includes top and bottom closure assemblies or clip assemblies 58, one above the trachea opening 36 and a second below the trachea opening 36. Wires 79 electrically communicate the clip assemblies 58 with the control assembly 22. The cervical collar system 10 also includes the detachable air/fluid hose or conduit 86, a port/valve (two-way) to connect for inflation the bladder member 16 with the detachable air hose.

In a preferred embodiment, a disconnect assembly 78 is positioned between the first pump assembly 24 and the collar assembly 12. The disconnect assembly 78 includes a connected configuration where the first pump assembly 24 is in electrical and fluid communication with the control assembly 22 and bladder member 16, respectively (or just fluid communication in the simple version) and a disconnected configuration where the first pump assembly 24 is not in electrical or fluid communication with the control assembly and bladder member.

Figure 12:
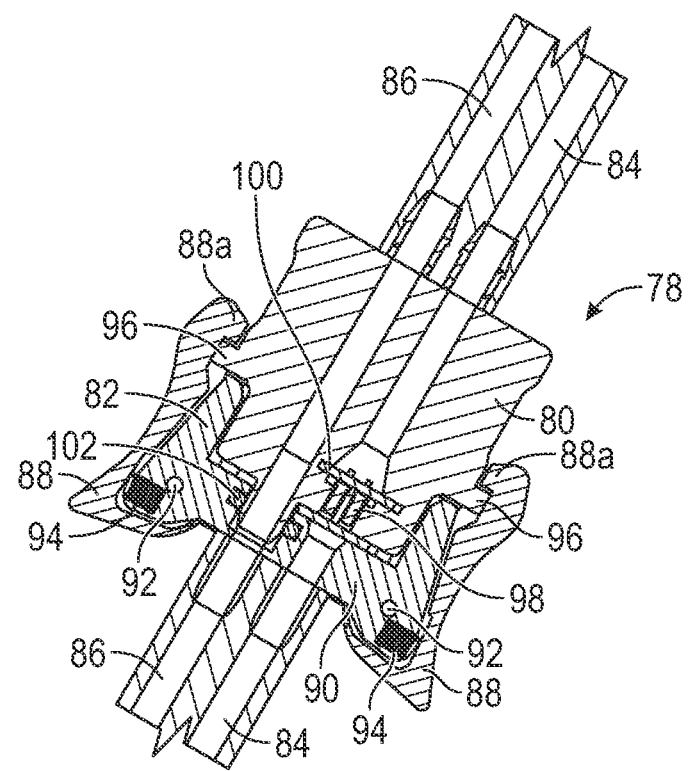
FIG. 12 is a cross-sectional view of the disconnect assembly.

As shown in FIG. 12, in a preferred embodiment, the disconnect assembly 78 includes a male member 80 and a female member 82 that meet with one another to provide both fluid and electrical connections through the disconnect assembly 78, thereby providing the first pump assembly 24 electrical communication with the control assembly 22 through the electrical conduit 84 and fluid communication with the bladder member 16 through the fluid conduit 86 (which may be routed to the manifold assembly 18 or directly into the bladder member 16). The female member 82 includes clamp wings 88 that are pivotably connected to the main body portion 90 of the female member 82 (see the pivot pins 92 in FIG. 12) and are biased by a spring 94 to a normal position. The clamp wings 88 include a hook portion 88a that is secured on a ledge member 96 on the male member 80. To disconnect the male member 80 from the female member 82 the clamp wings 88 are pinched or moved inwardly (compressing the springs 94), which pivots the hook portions 88a outwardly and off of the ledge members 96. To connect the male and female members, the male member 80 is pushed against the female member 82 and the ledge members 96 push and pivot the clamp wings 88 outwardly until the ledge members 96 pass the hook portion 88a. At that point, the springs 94 push outwardly to pivot the clamp wings inwardly to secure hook portions 88a on the ledge members 96.

It will be appreciated that the electrical connection may be made in a number of ways. An exemplary embodiment, the disconnect assembly 78 includes pogo pins 98 and a pad 100 that contact one another to make the electrical connection. This connection may be communicated to the control assembly 22 so that the system knows when the first pump assembly 24 is connected and disconnected. An o-ring 102 may be included to help establish the fluid connection. In another embodiment, the clamp wings may be on the male member and the ledge members may be on the female member.

Figure 13:
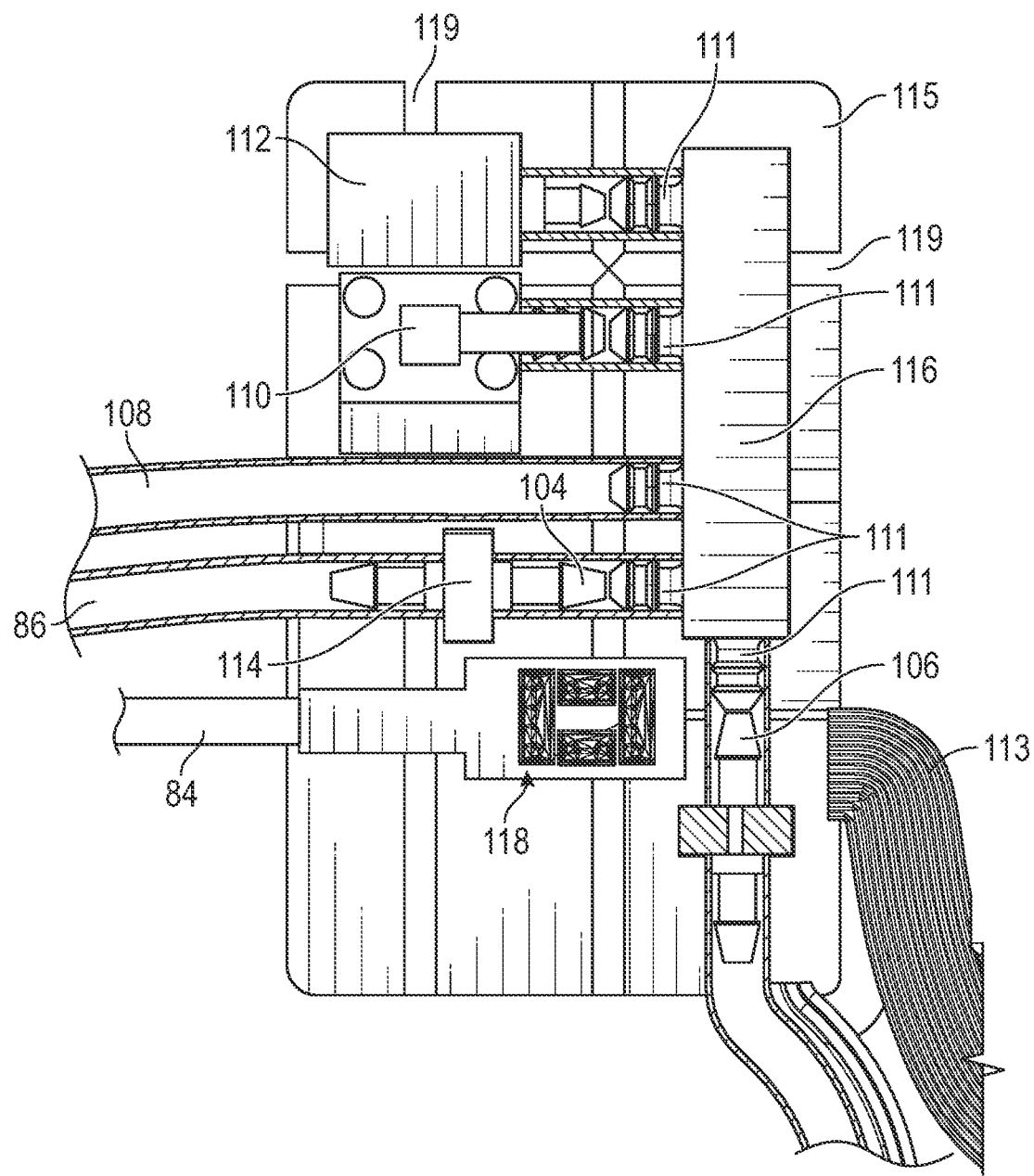
FIG. 13 is an elevational view of the manifold assembly.

FIG. 13 shows the manifold assembly 18. In an exemplary embodiment, the manifold assembly 18 receives air from the fluid conduit 86 from the first pump assembly 24 (see nozzle 104) and from the second pump assembly 20 (see nozzle 106). Air is routed to the bladder member 16 through a bladder conduit 108 (and into the bladder member 16 through port 109). Preferably, the manifold assembly 18 includes a pressure sensor 110, an air release valve 112, a check valve 114 so air does not escape back to the first pump assembly 24 and an air manifold 116 with five ports 111 thereon for routing air as necessary. The manifold assembly 18 also includes a PCB 118 that provides electrical connections and power so that there can be power routed to the pressure sensor 110, air release valve 112 and any other components needing power. There is also electrical communication (electrical and data connection) to the control assembly 22 (see wires 113).

In use, on command from the control assembly 22, the first and second pump assemblies 24 and 20 are switched on to inflate the bladder member 16 as quickly as possible. As discussed above, the control assembly 22 will only send the signal to inflate the bladder member 16 if the clip assemblies are properly connected (based on signals sent from the magnetic closure system). In a preferred embodiment, the system includes multiple pressure settings or predetermined pressure levels (for the bladder member), e.g., high, medium and low. In use, once the pressure sensor senses the desired pressure level has been reached, the pumps are switched off and the first pressure assembly 24 can be disconnected via the disconnect assembly 78. The pressure sensor 110 monitors the pressure within the bladder member 16 and the second pump assembly 20 may be switched on when necessary to maintain the pressure within the bladder member 16 at the predetermined pressure level. Furthermore, if after the first pump assembly 24 has been disconnected the operator desires to increase the pressure, the second pump assembly 20 will pump more air into the bladder member 16. If it is desired to decrease the pressure, the release valve 112 can be opened.

In a preferred embodiment, all of the housings 115 that house the manifold assembly 18, second pump assembly 20 and control assembly 22 may include notches 119 therein that allow the walls of the housing to move when the collar assembly is placed around the neck and the bladder member 16 is inflated. Preferably, the housings 115 are also made of a rubber or flexible plastic to allow flexibility and can be stitched to the liner member 30, as discussed above.

Figure 14:
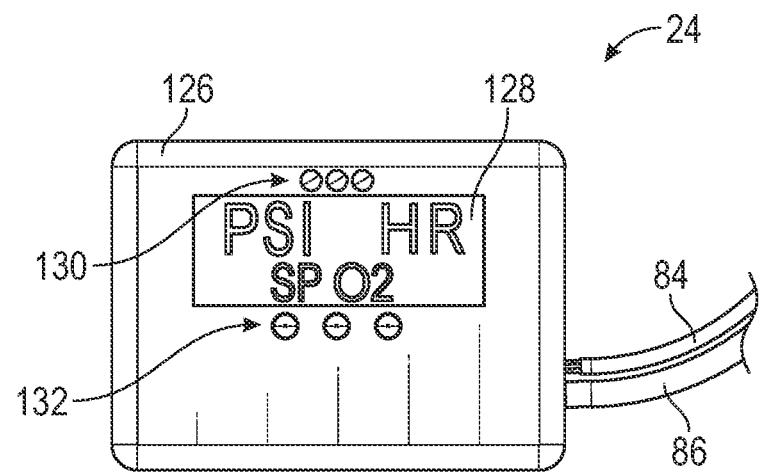
FIG. 14 is an elevational view of the first pump assembly and the user interface assembly.
Figure 14:
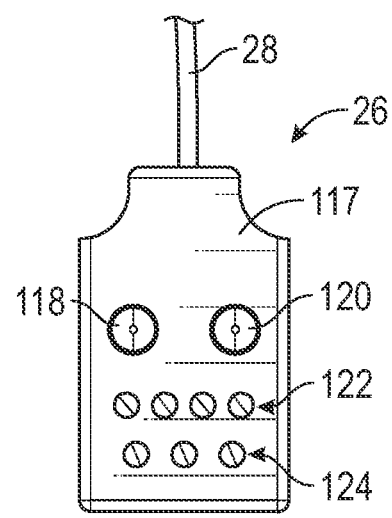

As shown in FIG. 14, the dongle or user interface assembly 26 may include buttons or switches and LEDs that are mounted or located on a housing 117. FIG. 14 shows seven LEDs and first and second buttons 118 and 120. In an exemplary embodiment, pushing both the first and second buttons shuts the cervical collar system 10 off and rapidly deflates or releases the air. Pushing the first button when 18 once causes the bladder member 16 to be inflated to the first pressure level, pushing the first button when 18 a second time increases the pressure to the second level, and pushing it a third time increases the pressure to the third level. Pushing the second button 120 after inflation past the first level decreases the pressure to the previous level or off. The top four LEDs 122 indicate battery level and the bottom three LEDs 124 are red, yellow and green, which indicate the status of the system. In an exemplary embodiment, when the green LED is on the system is ready to be inflated. When the red LED is on the system cannot be inflated (e.g., the magnetic closure system is not properly closed). When the yellow LED is on the system is in a caution state, e.g., the bladder is being inflated or some other event is occurring. The user interface assembly 26 may include the LED system readiness board tether/dongle member, an increase/decrease button system for inflation and rapid/emergency deflation by simultaneously pressing both buttons, a three color (red, yellow, green) system readiness LED light panel and a four blue LED light system for battery charge and readiness. The cervical collar system 10 may also include a USB Port, and a flex circuit connecting the magnetized closure system to the control assembly 22.

The first pump assembly 24 includes a housing 126 with a display screen 128 thereon, three LEDs 130 that operate similarly to the red, yellow and green LEDs on the user interface assembly 26 and three buttons 132. The buttons 132 can be used to operate different functions of the system. For example, one of the buttons 132 can be pressed to read the wearer's heart rate using the biometric sensor assembly (or other biometrics, such as blood pressure, ECG, $SPO_2$, etc.). The first pump assembly 24 (or the control assembly) may include a global positioning sensor and/or fall detection capability (as is described herein).

Figure 15:
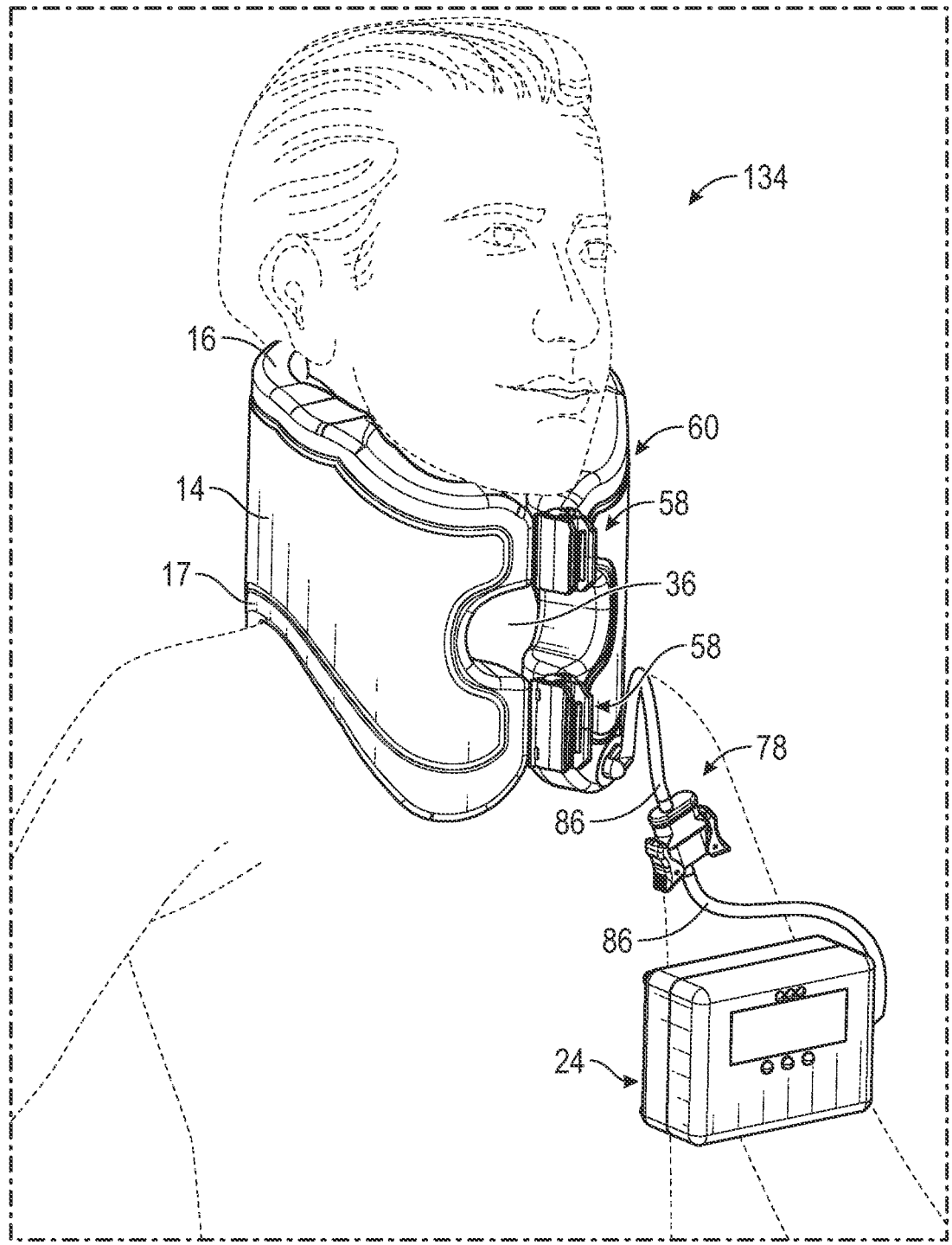
FIG. 15 is a front perspective view of a person wearing another cervical collar system in accordance with a preferred embodiment of the present invention.

FIG. 15 shows a version of the cervical collar system 134 that omits all electronics other than those associated with the first pump assembly 24. In this embodiment, the manifold assembly is omitted and the first pump assembly directs air directly into the bladder member 16. Furthermore, once the bladder member 16 is inflated and the first pump assembly 24 is disconnected, there is no metal in the assembly, thereby allowing the cervical collar system to remain on the user during medical procedures such as an MRI, CT Scan or x-ray. In another embodiment or version of the cervical collar system, the first pump assembly can be a $CO_2$ cartridge for inflating the bladder member. This version can be used, for example in an emergency situation in the military on the field of battle or other traumatic event where the person needs to be moved or extracted quickly.

It will be appreciated that in use, when the bladder member 16 is inflated, the bladder member 16 fills in the space using inflation and compression against the wall tension member between the wall member 14 and the wearer's neck, shoulders, upper back, jaw and other portions of the anatomy to secure the wearer's neck so that the vertebrae, bones and anatomy therein have little to no movement. These features are described in further detail above.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A cervical collar system comprising:
   a collar assembly that includes a bladder assembly received in a liner member, wherein the bladder assembly includes a wall member having an inner side and an outer side and a bladder member secured on the inner side of the wall member, wherein the collar assembly includes an open position and a closed position and is configured to be received on the neck of a wearer,
   a control assembly secured on an outer side of the liner member,
   a manifold assembly secured on an outer side of the liner member in electrical communication with the control assembly,
   a first pump assembly in fluid communication with the manifold assembly and in electrical communication with the control assembly,
   a second pump assembly secured on an outer side of the liner member, wherein the second pump assembly is in fluid communication with the manifold assembly,
   a user interface assembly in electrical communication with the control assembly,
   a disconnect assembly positioned between the first pump assembly and the collar assembly, wherein the disconnect assembly includes a connected configuration where the first pump assembly is in electrical communication with the control assembly and wherein the first pump assembly is in fluid communication with the manifold assembly and a disconnected configuration where the first pump assembly is not in electrical communication with the control assembly and the first pump assembly is not in fluid communication with the manifold assembly a closure system for maintaining the collar assembly in the closed position, wherein the closure system includes a first clip assembly that includes a barrel member secured to a first end of the bladder assembly and a clip member secured to the second end of the bladder assembly, wherein the closure system includes a second clip assembly that includes a barrel member secured to the first end of the bladder assembly and a clip member secured to the second end of the bladder assembly, wherein the collar assembly defines a trachea opening, wherein the first clip assembly is positioned above the trachea opening and the second clip assembly is positioned below the trachea opening, wherein the first clip assembly is in electrical communication with the control assembly, wherein the barrel member includes a first magnet member, wherein the clip member includes a second magnet member, wherein the control assembly will not signal inflation of the bladder member if the first and second magnet members are not in predetermined alignment, and a biometric sensor assembly secured to an inner side of the liner member and in electrical communication with the control assembly.

\* \* \* \* \*